United States Patent
Li et al.

(10) Patent No.: US 11,136,413 B2
(45) Date of Patent: *Oct. 5, 2021

(54) PDL-1 ANTIBODY, PHARMACEUTICAL COMPOSITION THEREOF, AND USES THEREOF

(71) Applicant: SICHUAN KELUN-BIOTECH BIOPHARMACEUTICAL CO., LTD., Sichuan (CN)

(72) Inventors: Baiyong Li, Guangdong (CN); Tongtong Xue, Sichuan (CN); Yu Xia, Guangdong (CN); Zhongmin Maxwell Wang, Guangdong (CN); Liang Xiao, Sichuan (CN); Lichun Wang, Sichuan (CN); Jingyi Wang, Sichuan (CN)

(73) Assignee: SICHUAN KELUN-BIOTECH BIOPHARMACEUTICAL CO., LTD., Sichuan (CN)

( * ) Notice: Subject to any disclaimer, the term of this patent is extended or adjusted under 35 U.S.C. 154(b) by 61 days.

This patent is subject to a terminal disclaimer.

(21) Appl. No.: 16/516,991

(22) Filed: Jul. 19, 2019

(65) Prior Publication Data

US 2020/0010570 A1    Jan. 9, 2020

Related U.S. Application Data

(63) Continuation of application No. 15/745,230, filed as application No. PCT/CN2017/075484 on Mar. 2, 2017, now Pat. No. 10,465,014.

(30) Foreign Application Priority Data

Mar. 4, 2016 (CN) .......................... 201610122117.6

(51) Int. Cl.
| | | |
|---|---|---|
| *C07K 16/46* | (2006.01) | |
| *C07K 14/705* | (2006.01) | |
| *C07K 16/28* | (2006.01) | |
| *A61K 39/395* | (2006.01) | |
| *A61K 47/68* | (2017.01) | |
| *A61P 35/02* | (2006.01) | |

(52) U.S. Cl.
CPC .......... *C07K 16/468* (2013.01); *A61K 39/395* (2013.01); *A61K 47/6803* (2017.08); *A61P 35/02* (2018.01); *C07K 14/70532* (2013.01); *C07K 16/2827* (2013.01); *C07K 16/2896* (2013.01); *C07K 16/462* (2013.01); *C07K 2317/24* (2013.01); *C07K 2317/33* (2013.01); *C07K 2317/51* (2013.01); *C07K 2317/515* (2013.01); *C07K 2317/52* (2013.01); *C07K 2317/565* (2013.01); *C07K 2317/76* (2013.01); *C07K 2317/92* (2013.01); *C07K 2319/30* (2013.01); *C07K 2319/50* (2013.01)

(58) Field of Classification Search
None
See application file for complete search history.

(56) References Cited

U.S. PATENT DOCUMENTS

| | | | |
|---|---|---|---|
| 7,943,743 B2 | 5/2011 | Korman et al. | |
| 8,383,796 B2 | 2/2013 | Korman et al. | |
| 8,557,777 B2 | 10/2013 | Perambakm et al. | |
| 2010/0203056 A1 | 8/2010 | Irving et al. | |
| 2011/0271358 A1 | 11/2011 | Freeman et al. | |
| 2016/0272708 A1 | 9/2016 | Chen | |

FOREIGN PATENT DOCUMENTS

| | | |
|---|---|---|
| CA | 2954868 A1 | 1/2016 |
| CN | 101104640 A | 1/2008 |
| CN | 103242448 A | 8/2013 |
| CN | 104250302 A | 12/2014 |
| CN | 104356236 A | 2/2015 |
| CN | 104558177 A | 4/2015 |
| CN | 104673895 A | 6/2015 |
| CN | 104673897 A | 6/2015 |
| CN | 104936982 A | 9/2015 |
| CN | 105175537 A | 12/2015 |
| CN | 105175544 A | 12/2015 |
| EA | 019344 B1 | 3/2014 |
| EP | 2133365 A2 | 12/2009 |
| EP | 2172219 B1 | 9/2013 |
| JP | 2008-544755 A | 12/2008 |
| JP | 2015-518826 A | 7/2015 |
| JP | 2015-519375 A | 7/2015 |

(Continued)

OTHER PUBLICATIONS

PCT/CN2017/075484, Jun. 2, 2017, International Search Report and Written Opinion.
EP17759275.5, Sep. 11, 2018, Extended European Search Report and Search Opinion.
EP17759275.5, Sep. 24, 2018, Replacement Extended European Search Report and Search Opinion.
AU2017226510, Oct. 16, 2018, Australian Office Action.
CA2987118, Aug. 23, 2018, Canadian Office Action.
CA2987118, May 22, 2019, Canadian Office Action.
CN201780002182.8, Jun. 13, 2018, Chinese Office Action.
CN201810647974.7, Feb. 14, 2019, Chinese Office Action.
CN201810647974.7, May 15, 2019, Chinese Office Action.
EP17759275.5, May 14, 2019, European Office Action.
JP2017-565750, May 15, 2018, Japanese Office Action.

(Continued)

*Primary Examiner* — Nelson B Moseley, II
(74) *Attorney, Agent, or Firm* — Wolf, Greenfield & Sacks, P.C.

(57) ABSTRACT

The present invention belongs to the field of tumor therapy and molecular immunology, and relates to a PDL-1 antibody, a pharmaceutical composition thereof and use thereof. In particular, the present invention relates to a PDL-1 monoclonal antibody or an antigen-binding fragment thereof, wherein the monoclonal antibody has a heavy chain variable region comprising CDRs as set forth in SEQ ID NOs: 15-17; and/or has a light chain variable region comprising CDRs as set forth in SEQ ID NOs: 18-20. The monoclonal antibody of the present invention can bind to PDL-1 specifically, and specifically remove immunosuppressive function of PDL-1 and activate T lymphocytes.

40 Claims, 16 Drawing Sheets

Specification includes a Sequence Listing.

(56) References Cited

FOREIGN PATENT DOCUMENTS

| JP | 2015-535691 A | 12/2015 |
|---|---|---|
| JP | 2016-504336 A | 2/2016 |
| WO | WO 2007/005874 A2 | 1/2007 |
| WO | WO 2008/083174 A3 | 12/2008 |
| WO | WO 2010/077634 A1 | 7/2010 |
| WO | WO 2010/102278 A1 | 9/2010 |
| WO | WO 2010/119704 A1 | 10/2010 |
| WO | WO 2011/066389 A1 | 6/2011 |
| WO | WO 2013/079174 A1 | 6/2013 |
| WO | WO 2013/173223 A1 | 11/2013 |
| WO | WO 2014/151006 A3 | 11/2014 |
| WO | WO 2015/112805 A1 | 7/2015 |
| WO | WO 2015/181342 A1 | 12/2015 |
| WO | WO 2015/195163 A1 | 12/2015 |
| WO | WO 2016/000619 A1 | 1/2016 |

OTHER PUBLICATIONS

KR10-2017-7036591, Dec. 19, 2018, Korean Office Action.
KR10-2017-7036591, Jun. 19, 2019, Korean Office Action.
RU2017145150, Oct. 22, 2018, Russian Office Action.
RU2017145150, Feb. 21, 2019, Russian Office Action.
International Search Report and Written Opinion dated Jun. 2, 2017 for Application No. PCT/CN2017/075484.
Extended European Search Report and Search Opinion dated Sep. 11, 2018 in connection with EP Patent Application No. 17759275.5.
Replacement Extended European Search Report and Search Opinion dated Sep. 24, 2018 in connection with EP Patent Application No. 17759275.5.
Australian Office Action issued in AU Patent Application No. 2017226510, dated Oct. 16, 2018.
Canadian Office Action issued in CA Patent Application No. 2987118, dated Aug. 23, 2018.
Canadian Office Action issued in CA Patent Application No. 2987118 dated May 22, 2019.
Chinese Office Action issued in CN Patent Application No. 2017-8002182.8, dated Jun. 13, 2018.
Chinese Office Action issued in CN Patent Application No. 2018-10647974.7, dated Feb. 14, 2019.
Chinese Office Action issued in CN Patent Application No. 2018-10647974.7, dated May 15, 2019.
European Office Action issued in EP Patent Application No. 17759275.5 dated May 14, 2019.
Japanese Office Action issued in JP Patent Application No. 2017-565750, dated May 15, 2018.
Korean Office Action issued in KR Patent Application No. 10-2017-7036591, dated Dec. 19, 2018.
Korean Office Action issued in KR Patent Application No. 10-2017-7036591, dated Jun. 19, 2019.
Russian Office Action issued in RU Patent Application No. 2017145150, dated Oct. 22, 2018.
Russian Office Action issued in RU Patent Application No. 2017145150, dated Feb. 21, 2019.
Deng et al., Preclinical pharmacokinetics, pharmacodynamics, tissue distribution, and tumor penetration of anti-PD-L1 monoclonal antibody, an immune checkpoint inhibitor. MABS. 2016;8(3):593-603. doi: 10.1080/19420862.2015.1136043. Epub Feb. 26, 2016.
Harmsen et al., Properties, production, and applications of camelid single-domain antibody fragments. Appl Microbiol Biotechnol. Nov. 2007;77(1):13-22. Epub Aug. 18, 2007. Review.
Huang et al., Clinical Research Progress of Anti PD-1PD-L1 Monoclonal Antibody in the Treatment of lung cancer. Chin. J. Lung Cancer. 2015;18(11):706-713.
Mariuzza, The Structural Basis of Antigen-Antibody Recognition. Ann. Rev. Biophys. Chem. 1987;16:139-59.
Rizvi et al., Activity and safety of nivolumab, an anti-PD-1 immune checkpoint inhibitor, for patients with advanced, refractory squamous non-small-cell lung cancer (CheckMate 063): a phase 2, single-arm trial. Lancet Oncol. Mar. 2015;16(3):257-265.
Rudikoff et al., Single amino acid substitution altering antigen-binding specificity. Proc Natl Acad Sci U S A. Mar. 1982;79(6):1979-83.

PDL-1 ANTIBODY, PHARMACEUTICAL COMPOSITION THEREOF, AND USES THEREOF

CROSS-REFERENCE TO RELATED APPLICATIONS

This application is a Continuation application of U.S. application Ser. No. 15/745,230, filed Jan. 16, 2018, which is the National Phase under 35 U.S.C. § 371 of PCT International Application No. PCT/CN2017/075484, filed Mar. 2, 2017, which claims priority of Chinese Patent Application No. 201610122117.6, filed Mar. 4, 2016. The entire contents of the aforementioned applications are hereby incorporated herein by reference.

TECHNICAL FIELD

The present invention pertains to the field of tumor therapy and molecular immunology, and relates to an anti-PDL-1 antibody, a pharmaceutical composition thereof and use thereof. In particular, the present invention relates to an anti-PDL-1 monoclonal antibody.

BACKGROUND ART

PD-1/PDL-1 signaling pathway is essential in the regulation of immune tolerance, microbial infection and tumor immune evasion. PD-1 (programmed cell death 1) is mainly expressed on T cells and other immune cells, and its ligand PDL-1 is highly expressed in many human tumor types. The presence of PDL-1 protein has been demonstrated by immunohistochemical analysis in human breast cancer, lung cancer, gastric cancer, colorectal cancer, esophageal cancer, ovarian cancer, cervical cancer, renal cell carcinoma, bladder cancer, pancreatic cancer, glioma and melanoma. Moreover, the expression level of PDL-1 is closely related to the clinical treatment and prognosis of a patient.

Blocking PD-1/PDL-1 signaling pathway can activate inhibited T cells, and induce activated T cells to attack cancer cells. Blocking PD-1/PDL-1 signaling can promote the proliferation of tumor antigen specific T cells which play a role in killing tumor cells, and then inhibit the growth of local tumor (Julie R et al., 2012, N Engl J Med. 366: 2455-2465); PDL-1 monoclonal antibody can up regulate the secretion of IFN-γ by tumor infiltrating CD8+ T cells, indicating that the blockade of the PD-1/PDL-1 signaling pathway plays a role in the immune response of tumor cells in order to induce the immune response (Blank C et al., 2006, Int. J. Cancer. 119:317-327).

In addition, PDL-1 can also bind to B7-1 in vivo. Studies have shown that the PDL-1/B7-1 complex is a negative signal for T cell activation, and the interaction can lead to the down-regulation of T cell surface activation markers, and inhibit the proliferation of T cells.

IL-2 (Interlukin-2) is a kind of lymphokine secreted by $T_h$ cells, and has a wide range of immune activities: ① stimulating the proliferation and differentiation of T cells; ② stimulating the generation of cytotoxic T lymphocytes; ③ stimulating the proliferation and differentiation of NK cells and enhance the activity of NK cells; ④ stimulating the generation of lymphokine activated killer cells (LAK cells) which is a type of tumor killing immune cells transformed from lymphocytes under the stimulation of IL-2 for 3-6 days in vitro. IFN-γ (Interferon-gamma) is produced by T cells, and it can inhibit the proliferation of tumor cells, increase the presentation of antigen by MHC, stimulate the expression of tumor necrosis factor, and prevent tumor angiogenesis. Recent studies reported that IFN-γ can suppress the ability of tumor cells to evade attacks from immune system by regulating the expression of Fas/FasL of tumor cells and enhancing the sensitivity of tumor cells to Fas mediated apoptosis, leading to the inhibition of the malignant tumor cells.

Currently, it is generally believed that antibodies targeting the PDL-1 pathway will lead to breakthrough in the treatment of a variety of tumors, including non-small cell lung cancer, renal cell carcinoma, ovarian cancer, melanoma (Homet M. B., Parisi G., et al., Anti-PD1 Therapy in Melanoma. Semin Oncol. 2015 June; 42(3):466-473), leukemia and anemia (Held S A, Heine A, et al., Advances in immunotherapy of chronic myeloid leukemia CML. Curr Cancer Drug Targets. 2013 September; 13(7):768-74).

At present, it is still necessary to develop a new anti-PDL-1 antibody with better binding affinity and blocking efficiency (PDL-1 to PD-1) to activate T lymphocytes.

CONTENTS OF THE INVENTION

By in-depth research and creative work, the inventors used recombinant PDL-1 expressed by mammalian cells as an antigen to immunize a mouse, and the spleen cells from the mouse were collected and fused with myeloma cells to generate hybridomas. By screening a large number of hybridomas, the following hybridoma cell strain was obtained: LT005, which was deposited in China Center for Type Culture Collection (CCTCC) on Aug. 4, 2015, with an accession number of CCTCC No. C2015133.

The inventors were surprised to find that the hybridoma cell strain LT005 could secrete monoclonal antibody (named as 5C10) that can specifically bind to PDL-1 and effectively block the binding of PDL-1 to PD-1. In addition, the inventors have also discovered two other monoclonal antibodies named as 5F10 and 9F6 that block the binding of PDL-1 to PD-1.

Furthermore, the inventors creatively produced humanized antibodies against PDL-1, named as 5C10H1L1, 5C10H1L2, 5C10H2L1 and 5C10H2L2 respectively.

Still furthermore, the inventors creatively mutated the constant region of 5C10H2L2 and generated 5C10H2L2-IgG1mt antibody, for which the ADCC (antibody-dependent cell-mediated cytotoxicity) and/or CDC (complement-dependent cytotoxicity) were effectively lowered.

Still furthermore, the inventors also found that the antibodies of this invention, especially 5C10, 5C10H1L1, 5C10H1L2, 5C10H2L1, 5C10H2L2, 5F10, 9F6 and 5C10H2L2-IgG1mt, can effectively bind and activate human T cells to induce the secretion of IFN-γ and IL-2, which indicates the potential for the prevention and treatment of lung cancer, melanoma, renal tumors, ovarian cancer, leukemia, and anemia.

Thus, the following invention is provided:

In one aspect, the invention relates to a monoclonal antibody or an antigen binding fragment thereof, wherein:

said monoclonal antibody has a heavy chain variable region comprising CDRs as set forth in SEQ ID NOs: 15-17, and/or has a light chain variable region comprising CDRs as set forth in SEQ ID NOs: 18-20;

or said monoclonal antibody has a heavy chain variable region comprising CDRs as set forth in SEQ ID NOs: 29-31, and/or has a light chain variable region comprising CDRs as set forth in SEQ ID NOs: 32-34;

or said monoclonal antibody has a heavy chain variable region comprising CDRs as set forth in SEQ ID NOs: 35-37, and/or has a light chain variable region comprising CDRs as set forth in SEQ ID NOs: 38-40.

The amino acid sequences of CDRs of 5C10, 5C10H1L1, 5C10H1L2, 5C10H2L1 or 5C10H2L2 are the same, as follows:

```
                                           (SEQ ID NO: 15)
        HCDR1: GFSLSNYD (SEQ ID NO: 16)
        HCDR2: IWTGGAT (SEQ ID NO: 17)
        HCDR3: VRDSNYRYDEPFTY (SEQ ID NO: 18)
        LCDR1: QSIGTN (SEQ ID NO: 19)
        LCDR2: YAS (SEQ ID NO: 20)
        LCDR3: QQSNSWPYT.
```

The amino acid sequences of CDRs of 5F10 are as follows:

```
                                           (SEQ ID NO: 29)
        HCDR1: GFDIKDTY (SEQ ID NO: 30)
        HCDR2: IDPADGNT (SEQ ID NO: 31)
        HCDR3: ARGLGAWFAS (SEQ ID NO: 32)
        LCDR1: QDITNS (SEQ ID NO: 33)
        LCDR2: YTS (SEQ ID NO: 34)
        LCDR3: QQGHTLPPT.
```

The amino acid sequences of CDRs of 9F6 are as follows:

```
                                           (SEQ ID NO: 35)
        HCDR1: GFNIKDTY (SEQ ID NO: 36)
        HCDR2: IDPANGNT (SEQ ID NO: 37)
        HCDR3: SRGPPGGIGEYIYAMDY (SEQ ID NO: 38)
        LCDR1: SSVSSSY (SEQ ID NO: 39)
        LCDR2: STS (SEQ ID NO: 40)
        LCDR3: HQYHRSPPT
```

The above CDRs can be obtained through technical approaches familiar to a person skilled in the art. For example, through analyzing amino acid sequence of the variable region for heavy chain or light chain using IMGT definition by VBASE2 database.

In some embodiments, said monoclonal antibody or antigen binding fragment thereof, wherein:

the heavy chain variable region has an amino acid sequence selected from SEQ ID NO: 2, SEQ ID NO: 6 and SEQ ID NO: 10, and/or the light chain variable region has an amino acid sequence selected from SEQ ID NO: 4, SEQ ID NO: 8 and SEQ ID NO: 12;

or the amino acid sequence of the heavy chain variable region is SEQ ID NO: 21, and/or the amino acid sequence of the light chain variable region is SEQ ID NO: 23;

or the amino acid sequence of the heavy chain variable region is SEQ ID NO: 25, and/or the amino acid sequence of the light chain variable region is SEQ ID NO: 27.

In some embodiments, said monoclonal antibody is selected from the following (1) to (7):

(1) The amino acid sequence of the heavy chain variable region is shown in SEQ ID NO: 2, and the amino acid sequence of the light chain variable region is shown in SEQ ID NO: 4 (5C10);

(2) The amino acid sequence of the heavy chain variable region is shown in SEQ ID NO: 6, and the amino acid sequence of the light chain variable region is shown in SEQ ID NO: 8 (5C10H1L1);

(3) The amino acid sequence of the heavy chain variable region is shown in SEQ ID NO: 10, and the amino acid sequence of the light chain variable region is shown in SEQ ID NO: 12(5C10H2L2 or 5C10H2L2-IgG1mt);

(4) The amino acid sequence of the heavy chain variable region is shown in SEQ ID NO: 6, and the amino acid sequence of the light chain variable region is shown in SEQ ID NO: 12 (5C10H1L2);

(5) The amino acid sequence of the heavy chain variable region is shown in SEQ ID NO: 10, and the amino acid sequence of the light chain variable region is shown in SEQ ID NO: 8 (5C10H2L1);

(6) The amino acid sequence of the heavy chain variable region is shown in SEQ ID NO: 21, and the amino acid sequence of the light chain variable region is shown in SEQ ID NO: 23 (5F10);

(7) The amino acid sequence of the heavy chain variable region is shown in SEQ ID NO: 25, and the amino acid sequence of the light chain variable region is shown in SEQ ID NO: 27 (9F6).

In some embodiments, the monoclonal antibody or an antigen binding fragment thereof, is selected from Fab, Fab', F(ab')$_2$, Fd, Fv, dAb, complementary determining region fragment, single chain antibody (e.g., scFv), humanized antibody, chimeric antibody or diabody.

In some embodiments, the monoclonal antibody or an antigen binding fragment thereof, binds to PDL-1 with EC$_{50}$ less than 100 nM, for example, less than 10 nM, 1 nM, 0.9 nM, 0.8 nM, 0.7 nM, 0.6 nM, 0.5 nM, 0.4 nM, 0.3 nM, 0.2 nM, 0.1 nM or less, preferably, the EC$_{50}$ is determined by indirect ELISA method.

In some embodiments, the monoclonal antibody or an antigen binding fragment thereof, wherein, the monoclonal antibody comprises a non-CDR region and the non-CDR region is derived from a species other than murine, for example, derived from a human antibody.

Preferably, the constant region of the monoclonal antibody is selected from constant region of human IgG1, IgG2, IgG3 or IgG4;

Preferably, the constant region of monoclonal antibody is a mutated human IgG1 constant region; more preferably, the mutated human IgG1 constant region has 1, 2 or 3 mutations at position 234, 235 and 237 in accordance with the EU numbering system, and the mutations are selected from: L234A, L235A and G237A.

In some embodiments, the monoclonal antibody or an antigen binding fragment thereof, wherein the monoclonal antibody is produced by hybridoma cell strain LT005, and the hybridoma cell strain LT005 is deposited in China Center for Type Culture Collection (CCTCC), and the accession number is CCTCC NO: C2015133.

Another aspect of the present invention relates to an isolated nucleic acid molecule A, which comprises a nucleotide sequence encoding a heavy chain variable region of an antibody, wherein:

said antibody has a heavy chain variable region comprising CDRs as set forth in SEQ ID NOs: 15-17;

preferably, the heavy chain of said antibody has an amino acid sequence of SEQ ID NO: 2, SEQ ID NO: 6 or SEQ ID NO: 10;

more preferably, said nucleic acid molecule has a nucleotide sequence of SEQ ID NO: 1, SEQ ID NO: 5 or SEQ ID NO: 9;

In another embodiment of the invention, said antibody has a heavy chain variable region comprising CDRs as set forth in SEQ ID NOs: 29-31, preferably, the heavy chain of said antibody has an amino acid sequence of SEQ ID NO: 21, more preferably, said nucleic acid molecule has a nucleotide sequence of SEQ ID NO: 22;

In another embodiment of the invention, said antibody has a heavy chain variable region comprising CDRs as set forth in SEQ ID NOs: 35-37, preferably, the heavy chain of said antibody has an amino acid sequence of SEQ ID NO: 25, more preferably, said nucleic acid molecule has a nucleotide sequence of SEQ ID NO: 26.

Further another aspect of the present invention relates to an isolated nucleic acid molecule B, which comprises a nucleotide sequence encoding a light chain variable region of an antibody, wherein:

said antibody has a light chain variable region comprising CDRs as set forth in SEQ ID NOs: 18-20, preferably, the light chain of said antibody has an amino acid sequence of SEQ ID NO: 4, SEQ ID NO: 8 or SEQ ID NO: 12;

more preferably, said nucleic acid molecule has a nucleotide sequence of SEQ ID NO: 3, SEQ ID NO: 7 or SEQ ID NO: 11;

In another embodiment of the invention, said antibody has a light chain variable region comprising CDRs as set forth in SEQ ID NOs: 32-34, preferably, the light chain of said antibody has an amino acid sequence of SEQ ID NO: 23, more preferably, said nucleic acid molecule has a nucleotide sequence of SEQ ID NO: 24;

In another embodiment of the invention, said antibody has a light chain variable region comprising CDRs as set forth in SEQ ID NOs: 38-40, preferably, the light chain of said antibody has an amino acid sequence of SEQ ID NO: 27, more preferably, said nucleic acid molecule has a nucleotide sequence of SEQ ID NO: 28.

Further another aspect of the present invention relates to an isolated nucleic acid molecule C, which comprises the previous nucleic acid molecule A and nucleic acid molecule B; optionally, the nucleic acid molecule C further comprises a linker sequence for connecting the nucleic acid molecule A and the nucleic acid molecule B.

Further another aspect of the present invention relates to a vector, which comprises the isolated nucleic acid molecule A, the isolated nucleic acid molecule B or the isolated nucleic acid molecule C.

Further another aspect of the present invention relates to a host cell, which comprises the isolated nucleic acid molecule A, the isolated nucleic acid molecule B or the isolated nucleic acid molecule C, or the vector.

As to the term "isolated nucleic acid molecule A", "isolated nucleic acid molecule B" or "isolated nucleic acid molecule C", the letter A, B or C were only used for the purpose of clarity, or for distinguishing, and the letter itself does not have special meaning.

Further another of the present invention relates to a method for preparing the monoclonal antibody or an antigen binding fragment thereof described above, which comprises the following steps: culturing the host cell of the invention under suitable conditions, and recovering the monoclonal antibody or an antigen binding fragment thereof from cell cultures.

Further another aspect of the present invention relates to a hybridoma cell strain LT005, which is deposited in China Center for Type Culture Collection (CCTCC), and the accession number is CCTCC NO: C2015133.

Another aspect of the present invention relates to a monoclonal antibody or an antigen binding fragment thereof that is capable of competitive binding to the antigen epitope of the antibody or a fragment secreted by hybridoma cell strain LT005. Preferably, the antibody or an antigen binding fragment thereof has any one of the following activities:

a drug that blocks PDL-1 binding to PD-1 or B7-1, a drug that regulates (e.g. down-regulates) PDL-1 activity or PDL-1 level, a drug that removes body immune suppression by PD-1 or PDL-1, or a drug that enhances the expression of IFN-γ and/or IL-2 in T lymphocytes.

Further another aspect of the present invention relates to a conjugate, comprising a monoclonal antibody or an antigen binding fragment thereof, and a coupling part, wherein the monoclonal antibody is any one of monoclonal antibodies or an antigen binding fragment thereof described in the invention, and the coupling part is a detectable label, preferably, the coupling part is a radioactive isotope, a fluorescent substance, a luminescent substance, a colored substance or an enzyme.

Further another aspect of the present invention relates to a kit, comprising the monoclonal antibody or an antigen binding fragment thereof, or the conjugate previous described above;

Preferably, the kit further comprises a secondary antibody that specifically recognizes the monoclonal antibody or an antigen binding fragment thereof; optionally, the secondary antibody is labeled with a detectable label, such as a radioactive isotope, a fluorescent substances, a luminescent substances, a colored substances or an enzyme.

Further another aspect of the present invention relates to a use of said monoclonal antibodies or an antigen binding fragments thereof or a conjugate thereof in the manufacture of a kit, and said kit is used to detect the existence or the level of PDL-1 in a sample.

Further another aspect of the present invention relates to a pharmaceutical composition, comprising the monoclonal antibody or an antigen binding fragment thereof or the conjugate of the present invention, optionally, further comprises a pharmaceutically acceptable carrier and/or an excipient.

Further another aspect of the present invention relates to a use of the monoclonal antibody or an antigen binding fragment thereof or the conjugate of the present invention in the manufacture of a medicament for preventing and/or treating and/or adjuvant treating and/or diagnosing a tumor or anemia; preferably, said tumor is selected from breast cancer, lung cancer, such as non-small cell lung cancer, liver cancer, gastric cancer, colorectal cancer such as colon cancer or rectal cancer, esophageal cancer, ovarian cancer, cervical cancer, renal cancer, prostate cancer, bladder cancer, pancreatic cancer, glioma, melanoma and leukemia.

Further another aspect of the present invention relates to a use of the monoclonal antibody or an antigen binding fragment thereof or the conjugate of the present invention in the manufacture of a drug for blocking PDL-1 binding to PD-1 or to B7-1, a drug for regulating (e.g. down-regulate) PDL-1 activity or PDL-1 level, a drug for removing immune suppression by PD-1 or by PDL-1, or a drug for enhancing the expression of IFN-γ and/or IL-2 by a T lymphocyte.

Further another aspect of the present invention relates to an in vivo or in vitro method, which comprises a step of administering to a cell with an effective amount of the monoclonal antibody or an antigen binding fragment thereof or the conjugates of the invention, and said method is:

a method for blocking PDL-1 binding to PD-1 or to B7-1, a method for regulating (e.g. down-regulate) PDL-1 activity or PDL-1 level, a method for removing immune suppression by PD-1 or by PDL-1, or a method for enhancing the expression of IFN-γ and/or IL-2 in a T lymphocyte.

In one embodiment of the present invention, said method is not for therapeutic purpose.

Further another aspect of the present invention relates to a method for treatment and/or prophylaxis of a tumor or anemia, comprising a step of administering to a subject with an effective amount of the monoclonal antibody or an antigen binding fragment thereof or the conjugate of the invention; preferably, the tumor is selected from breast cancer, lung cancer, such as non-small cell lung cancer, liver cancer, gastric cancer, colorectal cancer such as colon cancer or rectal cancer, esophageal cancer, ovarian cancer, cervical cancer, renal cancer, prostate cancer, bladder cancer, pancreatic cancer, glioma, melanoma and leukemia.

In the present invention, unless otherwise stated, the scientific and technical terms used in this invention shall have the meaning commonly understood by a person skilled in the art. In addition, the cell culture, molecular genetics, nucleic acid chemistry, and immunology related laboratory procedures used in this invention are the general procedures used in the relevant fields. Meanwhile, in order to better understand the invention, the definitions and interpretations of relevant terms are provided below.

As used in this invention, when referring to the amino acid sequence of PDL-1 protein (Programmed death-ligand 1, NCBI GenBank ID: NP_054862.1), including full-length PDL-1 protein, or the extracellular domain of PDL-1 (PDL-1ECD) or fragment containing PDL-1ECD; Fusion protein of PDL-1ECD, for example, fragment fused with IgG Fc from mice or human (mFc or hFc) is also included. Moreover, as understood by a person skilled in the art, PDL-1 protein would also include those into which mutations of amino acid sequence are naturally or artificially introduced (including but not limited to replacement, deletion and/or addition) without affecting the biological functions. Therefore, in the present invention, the term "PDL-1 protein" should include all such sequences, including the sequence list above and its natural or artificial variants. In addition, when the sequence fragment of PDL-1 protein is referred, it means not only the above sequence fragment, but also the corresponding sequence fragment of natural or artificial variants.

The term $EC_{50}$ is used herein to refer to concentration for 50% of maximal effect, i.e. the concentration that can cause 50% of the maximum effect.

The term "antibody" is used herein to refer to an immunoglobulin molecule that is usually composed of two pairs of polypeptide chains (each pair with a "Light" (L) chain and a "Heavy" (H) chain). Antibody light chains can be classified as κ and λ chain. The heavy chains can be classified as: μ, δ, γ, α and ε, and the corresponding antibodies are defined as IgM, IgD, IgG, IgA and IgE, respectively. In light and heavy chains, the variable and constant regions are linked by a "J" region of about 12 or more amino acids, and the heavy chain also comprises "D" regions of about 3 or more amino acids. Each heavy chain consists of a heavy chain variable region ($V_H$) and a heavy chain constant region ($C_H$). The heavy chain constant region consists of 3 domains ($C_H1$, $C_H2$ and $C_H3$). Each light chain consists of a light chain variable region ($V_L$) and a light chain constant region ($C_L$). The light chain constant region consists of one domain ($C_L$). The constant region of the antibody can mediate the binding of immunoglobulins to host tissue or factors, including various cells of immune system (e.g. effector cells) and the first component (C1q) of the classical complement system. The $V_H$ and $V_L$ regions can be further subdivided into highly variable regions (called Complementarity determining region, CDR) and conservative regions called framework (FR) which are distributed between CDRs. Each $V_H$ and $V_L$ consists of 3 CDRs and 4 FRs arranged in the following order: FR1, CDR1, FR2, CDR2, FR3, CDR3, FR4, from the amino terminus to the carboxyl terminus. The variable regions ($V_H$ and $V_L$) of the heavy chain and light chain form the antigen binding site. The assignment of amino acids of each region or domain followed the definition of *Kabat sequences of proteins of immunological interest* (National Institutes of Health, Bethesda, Md. (1987 and 1991)), or *Chothia & Lesk* (J. Mol. Biol. 196:901-917 (1987); Chothia et al. Nature 342:878-883 (1989)). The term "antibody" is not restricted by any specific antibody generation method. For example, it includes, in particular, recombinant antibodies, monoclonal antibodies and polyclonal antibodies. Antibodies can be different isotypes or subisotypes, e.g., IgG (e.g., IgG1, IgG2, IgG3 or IgG4 subtype), IgA1, IgA2, IgD, IgE or IgM antibodies.

The term "antigen binding fragment" of antibody is used herein to refer to the polypeptide containing full-length antibody fragment, it maintains the ability to specifically bind to the same antigen as the full-length antibody, and/or compete with full-length antibody for antigen specific binding, which is also known as the "antigen binding part". Often seen in the text of *Fundamental Immunology, Ch. 7* (Paul, W., ed., second edition, Raven Press, N.Y. (1989)), it is merged into this invention by reference, for all purpose. Antigen binding fragments can be produced by recombinant DNA technology or by enzymatic or chemical cleavage of intact antibodies. In some cases, antigen binding fragments include Fab, Fab', F (ab')$_2$, Fd, Fv, dAb, and complementarity determining region (CDR) fragments, single chain antibody fragment (e.g., scFv), chimeric antibodies, diabodies and such polypeptides, comprising at least a portion of the polypeptide which is sufficient to confer antigen specific binding capacity of antibody.

As is used in this invention, the term "Fd fragment" means an antibody fragment consisting of $V_H$ and $C_H1$ domains; the term "Fv fragment" means an antibody fragment consisting of the single chain $V_L$ and $V_H$ domains of the antibody; the term "dAb fragment" means an antibody fragment consisting of the $V_H$ domain (Ward et al., Nature 341:544-546 (1989)); the term "Fab fragment" means an antibody fragment consisting of $V_L$, $V_H$, $C_L$, and $C_H1$ domains; the term "F(ab')$_2$ fragment" means an antibody fragment containing two Fab fragments that are connected by disulfide bond bridges in the hinge region.

In some cases, the antigen binding fragment of the antibody is a single chain antibody (e.g., scFv), of which the $V_L$ and $V_H$ domains form monovalent molecules by a linker to form single polypeptide chain (for reference, e.g. Bird et al., Science 242:423-426 (1988) and Huston et al., Proc. Natl. Acad. Sci. USA 85:5879-5883 (1988)). Such scFv molecules may have a general structure: $NH_2$—$V_L$-Linker-$V_H$—COOH or $NH_2$—$V_H$-Linker-$V_L$—COOH. The appropriate recent technology of linker is made up of a repetitive GGGGS amino acid sequence or its variants. For example, (GGGGS)$_4$, but its variant may also be used (Holliger et al. (1993), Proc. Natl. Acad. Sci. USA 90: 6444-6448). Other linkers may be used in this invention are described by Alfthan et al. (1995), Protein Eng. 8:725-731, Choi et al. (2001) Eur. J. Immunol. 31: 94-106, Hu et al. (1996), Cancer Res. 56:3055-3061, Kipriyanov et al. (1999), J. Mol. Biol. 293:41-56 and Roovers et al. (2001), Cancer Immunol.

In some cases, the antigen binding fragment of the antibody is diabody, that is, a bivalent antibody, of which $V_H$ and $V_L$ are expressed in a single polypeptide chain, however, a very short linker was used to prevent paring of two domains from the same chain, thus, the domain is forced to pair with complementary domain of the other chain, and two antigen binding sites are formed (for reference, e.g. Holliger P. et al., Proc. Natl. Acad. Sci. USA 90:6444-6448 (1993), and Poljak R. J. et al., Structure 2:1121-1123 (1994)).

In other cases, the antibody antigen binding fragment is "bispecific antibody", defined by the first antibody (fragment) and second antibody (fragment) or antibody mimetic coupled by coupling arm, the coupling methods include but not limited to chemical reaction, gene fusion and enzymatic reaction. Antibody antigen binding fragments can be "multispecific antibodies" such as: Tri-specific antibody and tetra-specific antibody, the former can specifically bind to 3 different antigens, the latter can specifically bind to 4 different antigens. For example, the designed ankyrin repeat proteins (DARPin), linked to or associated with IgG antibodies, scFv-Fc antibody fragments, so as in CN104341529A; anti-IL-17a fynomer with anti-IL-6R antibody, so as in WO2015141862A1.

In other cases, the antibody antigen binding fragment is "bispecific antibody conjugate", defined by the first antibody (fragment) and second biological function fragment (non-antibody nor its mimetics) coupled by coupling arm, the coupling methods include but not limited to chemical reaction, gene fusion and enzymatic reaction, second biological function fragments include peptides with binding activity, proteins, polyethylene glycol (PEG), radionuclides, nucleic acids, small molecule toxins, receptors or ligands, etc., the conjugate retained activities of each fragment, thus double functions/bispecific.

Antigen binding fragment (e.g., above described antibody fragment) can be obtained from a given antibody (e.g., 5C10, 5C10H1L1, 5C10H1L2, 5C10H2L1 and 5C10H2L2 in this invention) by conventional technologies known to a person skilled in the art (for example, recombinant DNA or enzymatic or chemical cleavage methods) and the same specific screening method can be applied to antigen binding fragment as the intact antibody.

In this invention, unless specifically mentioned, the term "antibody" includes not only the intact antibody, but also the antigen binding fragment of the antibody.

The term "mAb" and "monoclonal antibody" is used herein to refer to a fragment from an antibody or antibody molecules in a highly homologous group, it is a group of identical antibody molecules, unless natural mutations occurred. Monoclonal antibodies are highly specific against single epitope on the antigen. The polyclonal antibodies are different from monoclonal antibodies, polyclonal antibodies usually contain at least 2 or more different antibodies that recognize different epitopes on the same antigen. Monoclonal antibodies can usually be obtained by hybridoma technology, which was first reported by Kohler et al (Nature, 256:495, 1975), but can also be obtained by recombinant DNA technology (see also U.S. Pat. No. 4,816,567).

The term "chimeric antibody" is used herein to refer to the antibody, of which part of light chain and/or heavy chain from an antibody (which can be derived from a specific species or belongs to a specific antibody class or subclass), and the other part of the light chain and/or heavy chain from another antibody (which may be derived from the same or different species or belongs to the same or different antibody classes or subclasses), Nevertheless, it still retains the binding activity to the target antigen (U.S. Pat. No. 4,816,567 to Cabilly et al.; Morrison et al., Proc. Natl. Acad. Sci. USA, 81:6851 6855 (1984)).

The term "humanized antibody" is used herein to refer to a human immunoglobulin (acceptor antibody) in which all or part of the CDRs are replaced by CDR regions from a non-human antibody (donor antibody), donor antibody may be a non-human (e.g., mouse, rat or rabbit) antibody with expected specificity, affinity or reactivity. In addition, amino acid residues of framework region (FR) of acceptor antibody can be replaced by amino acid from non-human antibodies, or amino acid of other antibodies in order to further improve the performance of the antibody. For more details about humanized antibodies, see examples, Jones et al., Nature, 321:522 525 (1986); Reichmann et al., Nature, 332:323 329 (1988); Presta, Curr. Op. Struct. Biol., 2:593 596 (1992); and Clark, Immunol. Today 21: 397 402 (2000).

Humanization method is based on the combination of one or more of the commonly used methods for humanization. For example, using the methods described below.

Humanization could be realized by CDR grafting. In this method, the CDR regions of mouse antibody was determined at first, and then the 6 CDRs of mouse heavy chain and light chain were grafted onto the human source template with high homology to the mouse FR region. The human source template can be selected from the original germline sequence (germline), such as germline sequence derived from the IMGT database, and can also be selected from mature antibody sequences, such as antibody sequence derived from the Gene bank. Back mutation can be introduced into CDR grafted antibody. Some amino acids of human template can be back mutated to amino acids of mouse template, so as to improve the affinity of antibody.

Humanization could also be realized by SDR grafting. In this method, the SDR regions of mouse antibody need to be determined at first. The SDR regions can be determined by methods such as alanine scanning. Then, the mouse SDR regions were grafted onto the human template with high homology to the mouse template. The human source template can be selected from the original germline sequence (germline), such as germline sequence derived from the IMGT database, and can also be selected from mature antibody sequences, such as antibody sequence derived from the Gene bank. Back mutation can be introduced into SDR grafted antibody. Some amino acids of human template can be back mutated to amino acids of mouse template, so as to improve the affinity of antibody. Tamura, M., D. E. Milenic, M. Iwahashi, E. Padlan, J. Schlom & S. V. Kashmiri: Structural correlates of an anti-carcinoma antibody: identification of specificity determining residues (SDRs) and development of aminimally immunogenic antibody variant by retention of SDRs only. J. Immunol., 164, 1432-41 (2000).

Humanization could also be realized by resurfacing. In this method, mouse antibody model could be obtained by computer homology modeling or protein crystal structure analysis. Amino acids on the surface of the antibody can be determined according to the model, and these amino acids were mutated to corresponding amino acids of human antibody. Amino acids of human antibodies with high frequency at the same site could be selected. Padlan, E. A.: A possible procedure for reducing the immunogenicity of antibody variable domains while preserving their ligand-binding properties. Mol. Immunol., 28, 489-98 (1991).

Humanization could also be realized by superhumanization. In this method, the CDR regions of mouse antibody were determined at first, then the human sequence with high homology to the 6 CDRs was chosen as the template onto which 6 mouse CDRs were grafted. The human source template can be selected from the original germline sequence (germline), such as germline sequence derived from the IMGT database, and can also be selected from mature antibody sequences, such as antibody sequence derived from the Gene bank. Back mutation can be introduced into CDR grafted antibody. Some amino acids of human template can be back mutated to amino acids of mouse template, so as to improve the affinity of antibody. Tan, P., D. A. Mitchell, T. N. Buss, M. A. Holmes, C. Anasetti & J. Foote: "Superhumanized" antibodies: reduction of immunogenic potential by complementarity determining region grafting with human germline sequences: application to an anti-CD28. J. Immunol., 169, 1119-25 (2002).

The term "separate" or "be separated" refer to the acquisition of something by artificial means at a natural state. If there is a kind of "separate" substances or ingredients in nature, it may be the natural environment in which the substances or ingredients settled has been changed, or they were separated under the natural environment, or both cases have occurred. For example, in a living animal, there is a natural polynucleotide or polypeptide which has not been separated, and the process that the high purity of the same polynucleotide or polypeptide isolated under this natural state is called being separated. The term "separate" or "be separated" does not exclude the presence of artificial or synthetic substances, and does not exclude the presence of other impurities that do not affect the activity.

The term "vector" is used herein to refer to a nucleic acid vehicle that can be inserted by a polynucleotide. Expression vector is a vector that can express the protein encoded by the inserted polynucleotide. The vector can be introduced into the host cells by transformation, transduction or transfection to express carried genetic elements in the host cells. Vectors are well known to a person skilled in the art, including but not limited to: plasmid; phagemid; cosmid; artificial chromosomes, such as yeast artificial chromosome (YAC), bacterial artificial chromosome (BAC) or P1 derived artificial chromosome (PAC); phage, such as λ phage or M13 phage and animal viruses. Animal viruses that can be used as vectors include but are not limited to retroviruses (including lentivirus), adenovirus, adeno-associated virus, herpes virus (such as herpes simplex virus), poxvirus, baculovirus, papillomavirus, papovaviruses (such as SV40). A vector may contain various express-control elements, including but not limited to promoter sequences, transcription initiation sequences, enhancer sequences, selection elements, and reporter genes. In addition, vector can also contain origin of replication.

The term "host cell" is used herein to refer to cells that can be used for vectors introduction, including but not limited to prokaryotic cells such as *Escherichia coli* or *Bacillus subtilis*, fungal cells such as yeast cells or *Aspergillus*, insect cells such as *Drosophila* cells S2 or Sf9, or animal cells such as fibroblasts, CHO cells, COS cells, NSO cells, HeLa cells, BHK cells, HEK 293 cells or human cells The term "specific binding" is used herein to refer to non-random binding reaction between two molecules, such as the reaction between an antibody and its targeting antigen. In some embodiments, specific binding of an antibody to an antigen (or antibody with specificity to an antigen) is used herein to refer to antibody with binding affinity ($K_D$) to antigen of less than $10^{-5}$ M, for example, less than $10^{-6}$ M, $10^{-7}$ M, $10^{-8}$ M, $10^{-9}$ M, $10^{-10}$ M or even less.

The term "$K_D$" is used herein to refer to the dissociation equilibrium constant of specific antibody-antigen interaction, which is used to describe the binding affinity between antibody and antigen. When the equilibrium dissociation constant is smaller, the antibody antigen binding is tighter, and the affinity between antibody and antigen is higher. Usually, antibody (For example, the monoclonal antibodies 5C10, 5C10H1L1, 5C10H1L2, 5C10H2L1 and 5C10H2L2 of this invention) binds to antigen (e.g. PDL-1 protein) with $K_D$ less than $10^{-5}$ M, for example, less than $10^{-6}$ M, $10^{-7}$ M, $10^{-8}$ M, $10^{-9}$ M, $10^{-10}$ M or even less as measured by the Fortebio molecular interaction detector.

The term "monoclonal antibody" and "mAb" have the same meaning and are used interchangeably; the term "polyclonal antibody" and "pAb" has the same meaning and are used interchangeable; the term "polypeptide" and "protein" have the same meaning and are used interchangeably. Also, in this invention, amino acids are usually represented by a single letter or a three-letter abbreviation accepted in this technical field. For example, alanine can be represented by A or Ala.

The term "hybridoma" and "hybridoma cell strain" are used interchangeably, and when terms "hybridoma" and "hybridoma cell strain" are mentioned, it also includes the subclone and progeny cells of hybridoma. For example, when hybridoma cell strain LT005 is mentioned, it also is used herein to refer to the subclone and progeny cells of hybridoma cell strain LT005.

The term "pharmaceutically acceptable vehicle and/or excipient" is used herein to refer to the vehicle and/or excipient which are compatible with recipients and active ingredient in pharmacology and/or physiology, which is well known in this technical field (see example Remington's Pharmaceutical Sciences. Edited by Gennaro AR, 19th ed. Pennsylvania: Mack Publishing Company, 1995), including but not limited to: pH modulators, surfactants, adjuvants, ionic strength enhancers. For example, pH modulators include but not limited to phosphate buffer saline; surfactants include but not limited to cationic, anionic or nonionic surfactants, such as Tween-80; ionic strength enhancer include but not limited to sodium chloride.

The term "adjuvant" is used herein to refer to a non-specific immune stimulating agent that enhances the immune response to an antigen or changes the type of immune response when it is delivered to the body previously or together with the antigen. There are many kinds of adjuvants, including but not limited to aluminum adjuvants (e.g., aluminum hydroxide), Freund's adjuvant (e.g. complete Freund's adjuvant and incomplete Freund's adjuvant), *Corynebacterium parvum*, lipopolysaccharide, cytokines, etc. Freund's adjuvant is the most commonly used adjuvant in animal experiments. Aluminum hydroxide adjuvant is used more often in clinical trials.

The term "effective dose" is used herein to refer to the amount sufficient to obtain or obtain at least some of the desired effect. For example, the effective dose of preventing disease, such as tumor, is used herein to refer to the amount that is sufficient to prevent, inhibit, or delay the occurrence of a disease, such as a tumor; The effective dose of treating a disease is used herein to refer to the amount that is sufficient to cure or at least partially inhibit the patient from having the disease and its complications. The determination of such effective dose is within the scope of skilled person of this technical field. For example, the effective dose of treating disease will depend on the disease severity, the overall state of the patient's immune system, the general conditions of the patient such as age, weight and sex, drug delivery, and also other treatment applied at the same time.

Advantages of the Present Invention

The monoclonal antibody 5C10 in the present is capable of binding to PDL-1 specifically, blocking PDL-1 from interacting with PD-1 very effectively, removing immune suppression to the immune system by PDL-1 specifically, and activating T lymphocytes.

BRIEF DESCRIPTION OF THE DRAWINGS

FIG. 22 5C10H1L1, 5C10H1L2, 5C10H2L2 or 5C10H2L1 competed with PD-1 for binding to PDL-1 (competitive ELISA).

FIG. 23 5C10H2L2 competed with B7-1 for binding to PDL-1 (competitive ELISA).

FIG. 24 5C10H2L2 increased IFN-γ secretion by blocking PDL-1 from interacting with PD-1.

FIG. 25 5C10H2L2 increased IL-2 secretion by blocking PDL-1 from interacting with PD-1.

DESCRIPTION OF THE PRESERVATION OF BIOLOGICAL MATERIAL

Hybridoma cell LT005 was deposited in China Center for Type Culture Collection (CCTCC) at Wuhan University (Postcode: 430072) on Aug. 4, 2015 with an accession number of CCTCC No. C2015133.

SPECIFIC MODELS FOR CARRYING OUT THE INVENTION

The following examples are put forth so as to provide those of ordinary skilled in the art with a complete disclosure and description of how to make and use the methods and compositions of the invention, and are not intended to limit the scope of what the inventors regard as their invention. The techniques or conditions not indicated in the examples can be carried out in accordance with the literature or product specifications. The reagents or instruments of which the manufacturers are not indicated are conventional products that can be purchased from the market.

BALB/c mice used in the present invention were purchased from the Guangdong Medical Lab Animal Center. The T cells used in the present invention were from Akeso Biopharma Co., Ltd.

Preparation Example 1

Recombinant Protein PDL-1ECD-mFc

1. Gene Synthesis of PDL-1ECD-mFc

The chimera gene was designed to comprise extracellular domain of PDL-1 (programmed cell death 1 ligand 1, NCBI GenBank ID: NP_054862.1), named PDL-1ECD, and Fc fragment (mFc) of mouse IgG. To improve the expression efficiency of the target gene in 293F cells, the nucleotide sequence was codon optimized and synthesize by GenScript Biotech Co., Ltd. In the scientific literature, PDL-1 and PD-L1 can be used interchangeably, and this invention unified use of PDL-1.

2. Generation of pUC57simple-PDL-1ECD-mFc Plasmid

The PDL-1ECD-mFc fusion gene synthesized by GenScript Biotech Co., Ltd. was cloned into the expression vector pUC57simple (supplied by GenScript Biotech Co., Ltd.) to obtain the pUC57simple-PDL-1ECD-mFc plasmid.

3. Construction of Recombinant Plasmid of pcDNA3.1-PDL-1ECD-mFc

The plasmid pUC57simple-PDL-1 ECD-mFc was subjected to enzyme digestion (Xba I and BamH I), and then to electrophoresis. The recovered PDL-1ECD-mFc gene fragment was cloned into pcDNA3.1 expression vector (purchased from Invitrogen) by ligation to obtain pcDNA3.1-PDL-1ECD-mFc plasmids. The ligation products were then transformed into the E. coli DH5a strain (purchased from TIANGEN BIOTECH CO. LTD.) according to instructions. Positive pcDNA3.1-PDL-1ECD-mFc colonies were obtained by screening, then were amplified with conventional method. The recombinant plasmid was extracted using a kit (TIANGEN BIOTECH (Beijing) CO. LTD.; DP103-03) according to the kit instructions.

4. The recombinant plasmid pcDNA3.1-PDL-1 ECD-mFc was transfected into 293F cells (Invitrogen) according to the lipofectamin transfection kit (Invitrogen).

Figure 1:
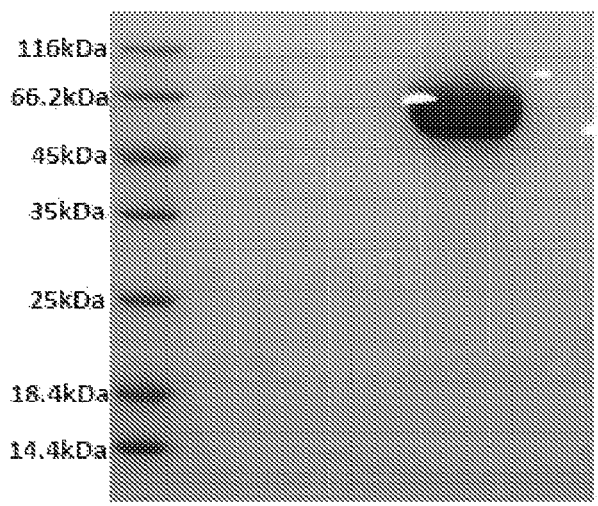
FIG. 1 SDS-PAGE analysis of PDL-1ECD-mFc fusion protein. The samples and loading amount thereof from left to right: Marker (10 μl); Sample loaded on chromatographic column (10 μl); Flow through (10 μl); Elution (10 μl).

5. Transfected 293F cells were cultured for 7 days. The culture supernatant containing the recombinant protein was then purified by high-speed centrifugation, microporous membrane vacuum filtration and HiTrap protein A HP column to obtain PDL-1ECD-mFc fusion protein, which was subjected to SDS-PAGE electrophoresis analysis with the addition of electrophoresis loading buffer under reduced conditions. As shown in FIG. 1, the molecular weight of target protein is about 53 kD.

Preparation Example 2

Preparation of Recombinant Protein PD-1-hFc

1. Gene Synthesis of PD-1-hFc

The chimera gene was designed to comprise extracellular domain of PD-1 (programmed cell death protein 1, NCBI GenBank ID: NP_005009.2) named PD-1ECD, and Fc fragment (hFc) of human IgG. To improve the expression efficiency of the target gene in 293F cells, the nucleotide sequence was codon optimized and synthesize by GenScript Biotech Co., Ltd.

2. Generation of pUC57simple-PD-1ECD-TEV-hFc Plasmid

The PD-1ECD-TEV-hFc gene was cloned into the expression vector pUC57simple (supplied by GenScript Biotech Co., Ltd.) to obtain the pUC57simple-PD-1ECD-TEV-hFc plasmid.

3. Construction of Plasmid pcDNA3.1-PD-1ECD-TEV-hFc

The plasmid pUC57simple-PD-1ECD-TEV-hFc was digested with enzyme (Xba I and BamH I). The purified PD-1ECD-TEV-hFc gene fragment was cloned into pcDNA3.1 expression vector (purchased from Invitrogen) to obtain pcDNA3.1-PD-1ECD-TEV-hFc which was transformed into E. coli DH5a strain (purchased from TIANGEN). Positive colonies were obtained by screening, which were then amplified by conventional E. coli DH5a culturing techniques, and the recombinant plasmid was extracted according to kit instruction (TIANGEN BIOTECH (Beijing) CO. LTD.; DP103-03).

4. The recombinant plasmid pcDNA3.1-PD-1ECD-TEV-hFc was transfected into 293F cells (Invitrogen) according to the lipofectamin transfection kit (Invitrogen).

Figure 2:
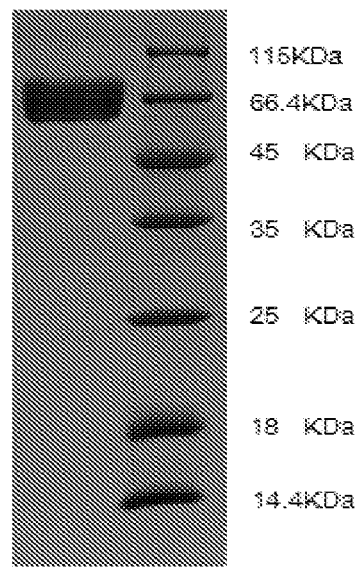
FIG. 2 SDS-PAGE analysis of PD-1-hFc fusion protein. The samples and loading amount thereof from left to right: Sample loaded on chromatographic column (10 μl); Marker (10 μl).

5. The 293F cells were transfected with pcDNA3.1-PD-1ECD-TEV-hFc and were cultured for 7 days. The culture supernatant containing the recombinant protein was then purified by high-speed centrifugation, microporous membrane vacuum filtration and Mabselect SuRe column to obtain PD-1ECD-TEV-hFc fusion protein, which was subjected to SDS-PAGE electrophoresis analysis with the addition of electrophoresis loading buffer under reduced conditions (FIG. 2).

Preparation Example 3

Preparation of Recombinant Protein B7-1-hFc

1. Gene Synthesis of B7-1-hFc

The chimera gene was designed to comprise extracellular domain of B7-1 (B7-1ECD; Cluster of Differentiation 80 (also CD80 and B7-1), NCBI GenBank ID: NP_005182.1) and Fc fragment (hFc) of human IgG. To improve the expression efficiency of the target gene in 293F cells, the nucleotide sequence was codon optimized and synthesize by GenScript Biotech Co., Ltd.

2. Generation of pUC57simple-B7-1ECD-hFc Plasmid

The B7-1ECD-hFc gene was cloned into the expression vector pUC57simple (supplied by GenScript Biotech Co., Ltd.) to obtain the pUC57simple-B7-1ECD-hFc plasmid.

3. Construction of Plasmid pcDNA3.1-B7-1ECD-hFc

The plasmid pUC57simple-B7-1ECD-hFc was digested with enzyme (Xba I and BamH I). The purified B7-1ECD-hFc gene fragment was cloned into pcDNA3.1 expression vector (purchased from Invitrogen) by ligation to obtain pcDNA3.1-B7-1ECD-hFc. The ligation products were then transformed into E. coli DH5a strain (purchased from TIANGEN). Colony screening was conducted and positive clones of pcDNA3.1-B7-1ECD-hFc were obtained, the clones were then amplified by conventional E. coli DH5a culturing techniques, and the recombinant plasmid was extracted according to kit instruction (TIANGEN BIOTECH(Beijing) CO. LTD.; DP103-03).

Figure 3:
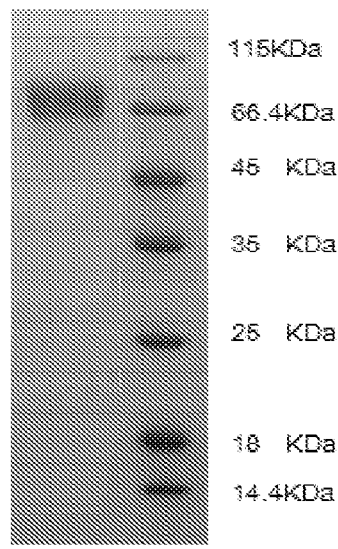
FIG. 3 SDS-PAGE analysis of B7-1-hFc fusion protein. The samples and loading amount thereof from left to right: Sample loaded on chromatographic column (10 μl); Marker (10 μl).

4. The recombinant plasmid pcDNA3.1-B7-1ECD-hFc was transfected into 293F cells (Invitrogen) according to the lipofectamin transfection kit (Invitrogen).
5. The 293-F cells were transfected with pcDNA3.1-PD-1ECD-TEV-hFc plasmids, and then were cultured for 7 days. The culture supernatant containing the recombinant protein was then purified by high-speed centrifugation, microporous membrane vacuum filtration and Mabselect SuRe column to obtain B7-1ECD-hFc fusion protein, which was subjected to SDS-PAGE electrophoresis analysis with the addition of electrophoresis loading buffer under reduced conditions (FIG. 3).

Example 1

Generation of Hybridoma Cell Strain LT005 and Monoclonal Antibody 5C10, 5F10 and 9F6

The recombinant PDL-1 ECD-mFc protein expressed by mammalian cells was used as immunogen to immunize mice. Splenocytes of immunized mice were harvested and fused with myeloma cells to generate hybridoma cells. After Screening through a large number of samples, a hybridoma cell strain LT005 was then obtained, which produced monoclonal antibody 5C10 that can specifically bind to PDL-1. Two other monoclonal antibodies 5F10 and 9F6 were also obtained in the present invention.

Details are as follows:

1. Generation of Hybridoma Cells

The recombinant PDL-1 ECD-mFc fusion protein obtained in Preparation Example 1 was used as immunogen to immunize BALB/C mice (Guangdong Medical Lab Animal Center.). Splenocytes of immunized mice were harvested and fused with mouse myeloma cells to generate hybridoma cells according to the general methods (e.g., Stewart, S. J., "Monoclonal Antibody Production", in Basic Methods in antibody Production and Characterization, Eds. G. C. Howard and D. R. Bethell, Boca Raton: CRC Press, 2000).

Indirect ELISA analysis was performed using PDL-1 ECD-mFc as coating antigen to obtain hybridoma cells producing antibodies that can specifically bind to PDL-1 ECD-mFc. Hybridoma cells were subsequently subjected to competitive ELISA, and those secreting monoclonal antibodies that compete with PD-1 (PD-1-hFc obtained from preparation example 2) in binding to PDL-1 were selected. And the stable hybridoma cell strain LT005 producing monoclonal antibody 5C10 was further obtained by limiting dilution.

Hybridoma cell strain LT005 was deposited in China Center for Type Culture Collection (CCTCC) at Wuhan University (Postcode: 430072) on Aug. 4, 2015 with an accession number of CCTCC No. C2015133.

Similarly, two additional hybridoma cell strain producing murine antibodies (named 5F10 and 9F6, respectively) were also obtained.

2. Preparation of Monoclonal Antibody 5C10, 5F10 and 9F6

The PDL-1-5C10 hybridoma cell strain was cultured in medium containing 10% (low IgG) fetal bovine serum (FBS) for 7 days and the cell culture supernatant was then collected and purified to get antibody 5C10.

Similarly, antibodies 5F10, 9F6 were prepared according to the method above.

3. SDS-PAGE Analysis of Antibody 5C10

Figure 4:
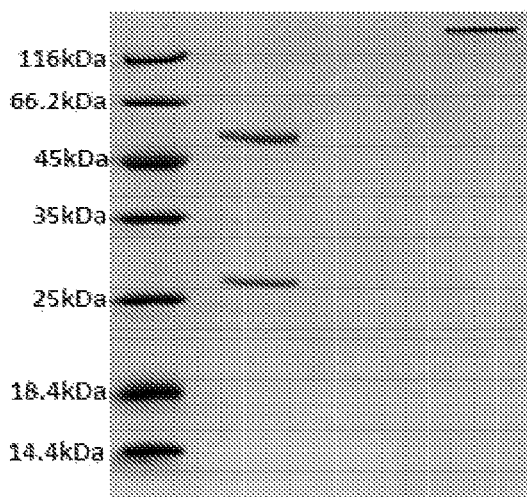
FIG. 4 SDS-PAGE analysis of antibody 5C10. The samples and loading amount thereof from left to right: Marker (10 μl); reduced protein sample (1 μg); Flow through of chromatographic column; Non-reduced protein sample (1 μl).
Figure 5:
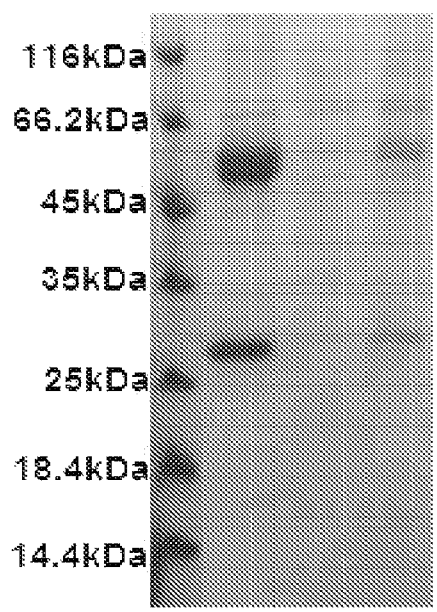
FIG. 5 SDS-PAGE analysis of 5C10H1L1 (humanized antibody of 5C10). The samples and loading amount thereof from left to right: Marker (10 μl); Elution of chromatographic column (10 μl); Flow through (10 μl); Sample loaded on chromatographic column (10 μl).
Figure 6:
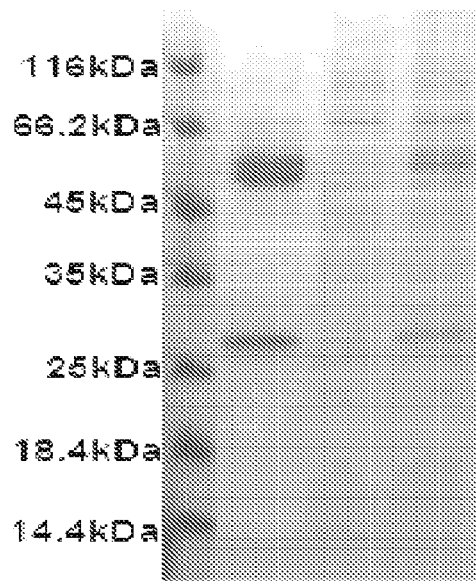
FIG. 6 SDS-PAGE analysis of 5C10H1L2 (humanized antibody of 5C10). The samples and loading amount thereof from left to right: Marker (10 μl); Elution of chromatographic column (10 μl); Flow through (10 μl); Sample loaded on chromatographic column (10 μl).
Figure 7:
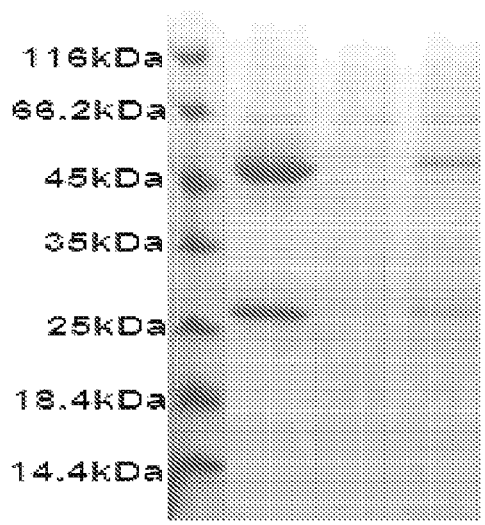
FIG. 7 SDS-PAGE analysis of 5C10H2L1 (humanized antibody of 5C10). The samples and loading amount thereof from left to right: Marker (10 μl); Elution of chromatographic column (10 μl); Flow through (10 μl); Sample loaded on chromatographic column (10 μl).
Figure 8:
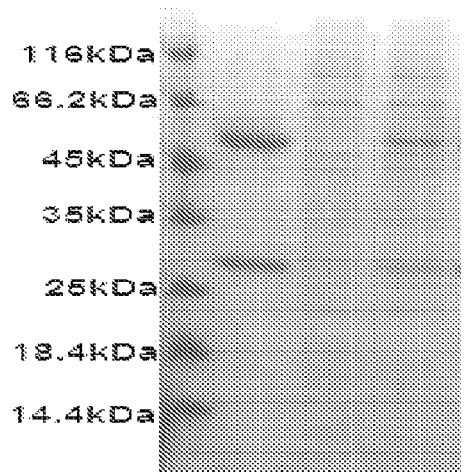
FIG. 8 SDS-PAGE analysis of 5C10H2L2 (humanized antibody of 5C10). The samples and loading amount thereof from left to right: Marker (10 μl); Elution of chromatographic column (10 μl); Flow through (10 μl); Sample loaded on chromatographic column (10 μl).

Samples of purified protein were added with reduced loading buffer and non-reduced loading buffer respectively. Together with the flow through from purification, all samples are boiled and loaded to SDS-PAGE gel for analysis. The results showed that the molecular weights of reduced proteins were about 50 kD and 25 kD, and the non-reduced protein was about 150 kD (FIG. 4)

4. Determination of Affinity, Competitive Affinity and Cellular Affinity on Murine Antibodies 5C10, 5F10 and 9F6:

The affinity of the antibody was determined by ELISA and competitive ELISA using the methods described in Example 9 and Example 13, respectively, and the affinity to the cells was determined by FACS using method described in Example 8.

The results are shown in Table 1.

TABLE 1

Affinity, competitive affinity and cellular affinity of murine antibodies 5C10, 5F10 and 9F6

| Antibody | Affinity by ELISA (nM) | Affinity by competitive ELISA (nM) | Cell affinity by FACS (nM; positive %) |
| --- | --- | --- | --- |
| 5C10 | 0.031 | 0.785 | 2.3, 100% |
| 5F10 | 0.029 | 0.838 | 1.48, 60.3% |
| 9F6 | 0.029 | 0.767 | 2.93, 80.2% |
| PCAB | 0.031 | 0.799-1.026 | 2.12, 70.5% |

The results showed that three murine antibodies were not inferior to the reference antibody PCAB (obtained in Example 5) in terms of affinity and competitive affinity. 5C10 had the best performance in the cell affinity and positive rate. Cell affinity of 5F10 is better than PCAB, and positive rate of 9F6 is better than PCAB.

Example 2

Acquisition of Sequences of Heavy Chains and Light Chains of Monoclonal Antibodies 5C10, 5F10 and 9F6

Total mRNA was extracted from the obtained hybridoma cell strain LT005 in Example 1 using RNA isolation kit (TIANGEN, DP430) according to the manufacturer's instruction.

The cDNA was synthesized using TransGen Biotech TransScript First-Strand cDNA Synthesis SuperMix kit according to manufacturer's instruction, and amplified by PCR. TA-cloning was performed on the PCR products according to the instructions from pEASY-T1 Cloning Kit (Transgen CT101). Products of TA-cloning are subjected to sequencing, and the results are as follows:

Nucleotide sequence encoding VH of antibody 5C10 (360 bp):

(SEQ ID NO: 1)
CAGGTGCAACTGAAGGAGTCAGGACCTGGCCTGGTGGCGCCCTCACAGAA

CCTGTCCATTACCTGCACTGTCTCTGGGTTCTCATTAAGCAACTATGATA

TAAGCTGGATTCGCCAGCCACCAGGAAAGGGTCTGGAGTGGCTCGGAGTA

ATATGGACTGGTGGAGCCACAAATTATAATTCAGCTTTCATGTCCAGACT

GAGCATCAGTAGGGACAACTCCAAGAGCCAAGTTTTCTTAAAAATGAACA

GTCTGCAAACTGATGACACAGCCATATATTACTGTGTGAGAGATTCGAAC

TATAGGTACGACGAGCCGTTTACTTACTGGGGCCAAGGGACTCTGGTCAC

TGTCTCTGCA

Amino acid sequence of VH of antibody 5C10 (120 aa):

(SEQ ID NO: 2)
QVQLKESGPGLVAPSQNLSITCTVSGFSLSNYDISWIRQPPGKGLEWLGV
IWTGGATNYNSAFMSRLSISRDNSKSQVFLKMNSLQTDDTAIYYCVRDSN
YRYDEPFTYWGQGTLVTVSA

Nucleotide sequence encoding VL of antibody 5C10 (318 bp):

(SEQ ID NO: 3)
GACATCTTGCTGACTCAGTCTCCAGCCATCCTGTCTGTGAGTCCAGGAGA
AAGAGTCAGTCTCTCCTGCAGGGCCAGTCAGAGCATTGGCACAAACATAC
ACTGGTTTCAGCAAAGAACAAATGGTTCTCCAAGGCTTCTCATAAAGTAT
GCTTCTGAGTCTATCTCTGGGATCCCTTCCAGGTTTAGTGGCAGTGGATC
AGGGACAGATTTTACTCTTAGCATCAACAGTGTGGAGTCTGAAGATATTG
CAGATTACTACTGTCAACAAAGTAATAGCTGGCCGTACACGTTCGGAGGG
GGGACCAAGCTGGAAATA

Amino acid sequence of VL of antibody 5C10 (106 aa):

(SEQ ID NO: 4)
DILLTQSPAILSVSPGERVSLSCRASQSIGTNIHWFQQRTNGSPRLLIKY
ASESISGIPSRFSGSGSGTDFTLSINSVESEDIADYYCQQSNSWPYTFGG
GTKLEI

Similarly, light and heavy chain sequences of monoclonal antibody 9F6 and 5F10 were obtained.

Amino acid sequence of VH of antibody 5F10 (117 aa):

(SEQ ID NO: 21)
EVQLQQSGAELVKPGASVKLSCTASGFDIKDTYIHWVKQRPEQGLEWIGR
IDPADGNTRYDPKFQDKTTTTTDTSSNTAHLQLSSLTSEDTAVYYCARGL
GAWFASWGQGTLVTVSA

Nucleotide sequence encoding VH of antibody 5F10 (351 bp):

(SEQ ID NO: 22)
GAGGTTCAGCTGCAGCAGTCTGGGGCAGAGCTTGTGAAGCCAGGGGCCTC
AGTCAAGTTGTCCTGCACAGCTTCTGGCTTCGACATTAAAGACACCTATA
TCCACTGGGTGAAGCAGAGGCCTGAACAGGGCCTGGAGTGGATTGGAAGG
ATTGATCCTGCGGACGGTAATACTAGGTATGACCCGAAGTTCCAGGACAA
GACCACTATAACAACCGACACATCCTCCAACACAGCCCACCTGCAGCTCA
GCAGCCTGACATCTGAGGACACTGCCGTCTATTACTGTGCTAGAGGCCTC
GGAGCTTGGTTTGCTTCCTGGGGCCAAGGGACTCTGGTCACTGTCTCTGC
A

Amino acid sequence of VL of antibody 5F10 (106 aa):

(SEQ ID NO: 23)
DIQMTQTTSSLSASLGDRVTISCRASQDITNSLNWYQQKPDGTVKLLIHY
TSRLHSGVPSRFSGSGSGTDYSLTISNLEQEDIATYFCQQGHTLPPTFGG
GTKLEI

Nucleotide sequence encoding VL of antibody 5F10 (318 bp):

(SEQ ID NO: 24)
GATATCCAGATGACACAGACTACATCCTCCCTGTCTGCCTCTCTGGGAGA
CAGAGTCACCATCAGTTGCAGGGCAAGTCAGGACATTACCAATTCCTTAA
ACTGGTATCAGCAGAAACCAGATGGAACTGTTAAACTCCTGATCCACTAC
ACATCAAGATTACACTCAGGAGTCCCATCAAGGTTCAGTGGCAGTGGGTC
TGGAACAGATTATTCTCTCACCATTAGCAACCTGGAGCAAGAAGATATTG
CCACTTACTTTTGCCAACAGGGTCATACGCTTCCTCCGACGTTCGGTGGA
GGCACCAAGCTGGAAATC

Amino acid sequence of VH of antibody 9F6 (124 aa):

(SEQ ID NO: 25)
EVQLQQSGAELVKPGASVKLSCTASGFNIKDTYMYWVKQRPEQGLEWIGR
IDPANGNTKYDPKFQGKATITADTSANTAYLQLSSLTSEDTAVYYCSRGP
PGGIGEYIYAMDYWGQGTSVTVSS

Nucleotide sequence encoding VH of antibody 9F6 (372 bp):

(SEQ ID NO: 26)
GAGGTTCAGCTGCAGCAGTCTGGGGCAGAGCTTGTGAAGCCAGGGGCCTC
AGTCAAGTTGTCCTGCACAGCTTCTGGCTTCAACATTAAAGACACCTATA
TGTACTGGGTGAAGCAGAGGCCTGAACAGGGCCTGGAGTGGATTGGAAGG
ATTGATCCTGCGAATGGTAATACTAAATATGACCCGAAGTTCCAGGGCAA
GGCCACTATAACAGCAGACACATCCGCCAACACAGCCTACCTGCAGCTCA
GCAGCCTGACATCTGAGGACACTGCCGTCTATTACTGTTCTAGAGGCCCT
CCAGGAGGTATCGGCGAGTATATCTATGCTATGGACTACTGGGGTCAAGG
AACCTCAGTCACCGTCTCCTCA

Amino acid sequence of VL of antibody 9F6 (107 aa):

(SEQ ID NO: 27)
QIVLTQSPAIMSASLGERVTMTCTASSSVSSSYLHWYQQKPGSSPKLWIY
STSNLASGVPARFSGSGSGTSYSLTISSMEAEDAATYYCHQYHRSPPTFG
GGTKLEI

Nucleotide sequence encoding VL of antibody 9F6 (321 bp):

(SEQ ID NO: 28)
CAAATTGTTCTCACCCAGTCTCCAGCAATCATGTCTGCATCTCTAGGGGA
ACGGGTCACCATGACCTGCACTGCCAGCTCAAGTGTAAGTTCCAGTTACT
TGCACTGGTACCAGCAGAAGCCAGGATCCTCCCCCAAACTCTGGATTTAT
AGCACATCCAACCTGGCTTCTGGAGTCCCAGCTCGCTTCAGTGGCAGTGG
GTCTGGGACCTCTTACTCTCTCACAATCAGCAGCATGGAGGCTGAAGATG
CTGCCACTTATTACTGCCACCAGTATCATCGTTCCCCACCCACGTTCGGT
GGAGGCACCAAGCTGGAAATC

Example 3

Design of Light and Heavy Chain Sequences of Humanized Antibody 5C10H1L1, 5C10H1L2, 5C10H2L1 and 5C10H2L2

The three dimensional crystal structure of PDL-1 protein (PDB Code 3BIK, Lin, DY et. al., PNAS USA 105(8): 3011-6 (2008)) and 5C10 structure obtained by computational modeling based on sequence in Example 2, were used for mutation design, mutated antibody variable region sequences of 5C10H1L1, 5C10H1L2, 5C10H2L1, 5C10H2L2 were then generated (constant region of heavy chain was Ig gamma-1 chain C region, ACCESSION: P01857; constant region of light chain was Ig kappa chain C region, ACCESSION: P01834). The sequences of variable region are shown below:

1. The Sequences of Light and Heavy Chain of Humanized Monoclonal Antibody 5C10H1L1

Nucleotide sequence of VH of antibody 5C10H1L1 (360 bp):

(SEQ ID NO: 5)
CAGGTCCAGCTGCAGGAGTCAGGCCCCGGCCTGGTGAAGCCCAGTGAGAA

CCTGTCAATCACCTGCACAGTCTCTGGCTTCTCACTGAGCAATTACGACA

TCAGTTGGATTCGACAGCCCCCTGGAAAGGGCCTGGAATGGCTGGGCGTG

ATCTGGACAGGCGGGGCAACTAACTATAATCCAGCCTTTAAAAGCCGGCT

GACCATTTCCAGAGACAACTCCAAGTCTCAGGTGTCTCTGAAAATGAGCT

CCCTGCAGGCCGCTGATACCGCTGTGTACTATTGTGTCAGGGACAGCAAT

TACCGCTATGATGAGCCCTTCACATACTGGGGCAGGGAACTCTGGTGAC

CGTCTCTAGT

Amino acid sequence of VH of antibody 5C10H1L1 (120 aa):

(SEQ ID NO: 6)
QVQLQESGPGLVKPSENLSITCTVSGFSLSNYDISWIRQPPGKGLEWLGV

IWTGGATNYNPAFKSRLTISRDNSKSQVSLKMSSLQAADTAVYYCVRDSN

YRYDEPFTYWGQGTLVTVSS

Nucleotide sequence encoding VL of antibody 5C10H1L1 (321 bp):

(SEQ ID NO: 7)
GAAATCGTGCTGACACAGAGCCCTGACACACTGAGCGTGACTCCCAAGGA

GAAAGTCACCCTGACATGCCGGGCATCACAGAGCATCGGAACAAACATTC

ACTGGTTCCAGCAGAGACCAGGCCAGAGCCCCAAGCTGCTGATCAAATAC

GCCTCCGAATCTATCAGTGGCATTCCTTCCCGATTCTCAGGCAGCGGGTC

CGGAACCGACTTTACTCTGACCATTAACTCTGTGGAGGCTGAAGATGCCG

CTACATACTATTGCCAGCAGTCTAATAGTTGGCCTTATACCTTCGGCCAG

GGGACAAAGCTGGAGATCAAA

Amino acid sequence of VL of antibody 5C10H1L1 (107 aa):

(SEQ ID NO: 8)
EIVLTQSPDTLSVTPKEKVTLTCRASQSIGTNIHWFQQRPGQSPKLLIKY

ASESISGIPSRFSGSGSGTDFTLTINSVEAEDAATYYCQQSNSWPYTFGQ

GTKLEIK

2. The Sequences of Light and Heavy Chain of Humanized Monoclonal Antibody 5C10H2L2

Nucleotide sequence encoding VH of antibody 5C10H2L2 (360 bp):

(SEQ ID NO: 9)
CAGGTCCAGCTGCAGGAGTCCGGCCCCGGCCTGGTGAAGCCCTCCGAGAC

ACTGTCTATCACCTGCACAGTCAGCGGCTTCTCACTGAGCAACTACGACA

TCTCCTGGATTCGACAGCCCCCTGGAAAGGGCCTGGAATGGCTGGGCGTG

ATCTGGACAGGCGGGGCAACTAACTATAATCCAGCCCTGAAATCTCGGCT

GACTATTAGTAGAGACAACTCAAAGAATCAGGTGTCCCTGAAAATGAGCT

CCGTCACCGCCGCTGATACAGCTGTGTACTATTGTGTCAGGGACAGCAAT

TACCGCTATGATGAGCCCTTTACCTACTGGGGGCAGGGAACTCTGGTGAC

CGTCTCTAGT

Amino acid sequence of VH of antibody 5C10H2L2 (120 aa):

(SEQ ID NO: 10)
QVQLQESGPGLVKPSETLSITCTVSGFSLSNYDISWIRQPPGKGLEWLGV

IWTGGATNYNPALKSRLTISRDNSKNQVSLKMSSVTAADTAVYYCVRDSN

YRYDEPFTYWGQGTLVTVSS

Nucleotide sequence encoding VL of antibody 5C10H2L2 (321 bp):

(SEQ ID NO: 11)
GAAATCGTGCTGACACAGTCTCCTGATACCCTGAGCGTGACTCCCAAGGA

GAAAGTCACCCTGACATGCAGGGCATCACAGAGCATCGGAACAAACATTC

ACTGGTTCCAGCAGAAGCCAGGCCAGAGCCCCAAGCTGCTGATCAAATAC

GCCTCCGAATCTATTAGTGGAGTGCCTTCCCGCTTCTCAGGCAGCGGGTC

CGGAACCGACTTTACTCTGACCATCAACTCTGTGGAGGCTGAAGATGCCG

CTACATACTATTGCCAGCAGTCTAATAGTTGGCCTTATACCTTCGGCCAG

GGGACAAAGCTGGAGATCAAA

Amino acid sequence of VL of antibody 5C10H2L2 (107 aa):

(SEQ ID NO: 12)
EIVLTQSPDTLSVTPKEKVTLTCRASQSIGTNIHWFQQKPGQSPKLLIKY

ASESISGVPSRFSGSGSGTDFTLTINSVEAEDAATYYCQQSNSWPYTFGQ

GTKLEIK

3. The Sequences of Light and Heavy Chain of Humanized Monoclonal Antibody 5C10H1L2

Nucleotide sequence encoding VH of antibody 5C10H1L2: SEQ ID NO: 5

Amino acid sequence of VH of antibody 5C10H1L2: SEQ ID NO: 6

Nucleotide sequence encoding VL of antibody 5C10H1L2: SEQ ID NO: 11

Amino acid sequence of VL of antibody5C10H1L2: SEQ ID NO: 12

4. The Sequences of Light and Heavy Chain of Humanized Monoclonal Antibody 5C10H2L1

Nucleotide sequence encoding VH of antibody 5C10H2L1: SEQ ID NO: 9

Amino acid sequence of VH of antibody 5C10H2L1: SEQ ID NO: 10

Nucleotide sequence encoding VL of antibody 5C10H2L1: SEQ ID NO: 7

Amino acid sequence of VL of antibody 5C10H2L1: SEQ ID NO: 8

Example 4

Preparation of 5C10 Humanized Antibody 5C10H1L1, 5C10H1L2, 5C10H2L1, 5C10H2L2 and SDS-PAGE Analysis Thereon The cDNA of heavy chain (VH: SEQ ID NO: 5 or SEQ ID NO: 9; CH: hIgG1) and light chain (VL: SEQ ID NO: 7 or SEQ ID NO: 11; CL: human kappa sequence) for 5C10H1L1, 5C10H1L2, 5C10H2L1 and 5C10H2L2 were cloned into vector pUC57simple (GenScript Biotech Co., Ltd) to obtain pUC57simple-5C10H1, pUC57simple 5C10L1, pUC57simple-5C10H2 and pUC57simple-5C10L2 plasmid.

The sequences were further cloned into vector pcDNA3.1 according to the method described in Preparation example 1. Recombinant plasmids were extracted and co-transfected into 293F cells. After being cultured for 7 days, the culture supernatant was then purified by high-speed centrifugation, microporous membrane vacuum filtration and HiTrap protein A HP column.

Samples of purified protein are added with reduced and non-reduced loading buffer separately, all samples are boiled and loaded on SDS-PAGE gel for analysis. The results are showed in as FIG. 5, FIG. 6, FIG. 7 and FIG. 8, wherein the reduced sample has two bands on the gel, corresponding to 50 kD and 25 KD bands on protein marker respectively, and the non-reduced protein has a band at 150 kD.

Example 5

Analysis of Binding Kinetic Parameters of Humanized Antibody 5C10H2L2

The binding kinetic parameters of the humanized antibody 5C10H2L2 to antigen PDL-1 (NCBI GenBank ID: NP_054862.1, nucleotide sequence: SEQ ID NO: 13; amino acid sequence: SEQ ID NO: 14) were determined by Fortebio.

1. Sample Preparation (1) The PDL-1-mFc protein was prepared by the method described in Preparation Example 1, and then the PDL-1-mFc protein was digested with TEV protease and purified by column chromatography to obtain PDL-1 antigen.

The DNA sequence of PDL-1 (870 bp):

(SEQ ID NO: 13)
ATGAGGATTTTCGCCGTCTTTATCTTTATGACCTACTGGCATCTGCTGAA

CGCTTTTACTGTGACCGTCCCCAAGGATCTGTATGTGGTGGAGTACGGAA

GCAACATGACTATCGAGTGCAAGTTCCCCGTGGAAAAACAGCTGGACCTG

GCCGCTCTGATTGTCTATTGGGAGATGGAAGATAAGAATATCATTCAGTT

TGTGCACGGCGAGGAAGACCTGAAAGTCCAGCATAGCTCCTACAGGCAGC

GCGCCCGACTGCTGAAGGATCAGCTGTCCCTGGGGAACGCAGCCCTGCAG

ATCACCGACGTGAAACTGCAGGATGCTGGAGTCTACAGGTGCATGATCTC

TTACGGCGGGGCTGATTATAAGCGCATTACAGTGAAAGTCAATGCACCTT

ATAACAAGATCAATCAGAGAATTCTGGTGGTCGACCCAGTGACCAGTGAG

CACGAACTGACATGTCAGGCTGAGGGCTACCCCAAGGCAGAAGTGATCTG

GACCTCTAGTGATCATCAGGTCCTGTCAGGGAAAACCACAACTACCAACA

GCAAGCGAGAGGAAAAACTGTTCAATGTGACATCCACTCTGAGGATCAAC

ACAACTACCAATGAGATTTTCTATTGCACTTTTCGGAGACTGGACCCTGA

GGAAAACCACACCGCAGAGCTGGTCATCCCAGAACTGCCACTGGCACACC

CACCTAATGAGCGAACACACCTGGTCATCCTGGGAGCCATTCTGCTGTGC

CTGGGCGTCGCTCTGACTTTCATTTTTCGGCTGAGAAAGGGGCGGATGAT

GGACGTGAAAAAGTGTGGCATTCAGGATACTAACTCAAAAAAGCAGTCCG

ATACCCATCTGGAAGAAACC

The amino acid sequence of PDL-1 (290 aa):

(SEQ ID NO: 14)
MRIFAVFIFMTYWHLLNAFTVTVPKDLYVVEYGSNMTIECKFPVEKQLDL

AALIVYWEMEDKNIIQFVHGEEDLKVQHSSYRQRARLLKDQLSLGNAALQ

ITDVKLQDAGVYRCMISYGGADYKRITVKVNAPYNKINQRILVVDPVTSE

HELTCQAEGYPKAEVIWTSSDHQVLSGKTTTTNSKREEKLFNVTSTLRIN

TTTNEIFYCTFRRLDPEENHTAELVIPELPLAHPPNERTHLVILGAILLC

LGVALTFIFRLRKGRMMDVKKCGIQDTNSKKQSDTHLEET (2) Preparation of the Positive Control Antibody HpLp and PCAB In the present invention, HpLp or PCAB is selected as the positive control, wherein HpLp is Atezolizumab (trade name Tecentriq®) on the market, and PCAB is PDL-1 antibody in clinical trial.

Atezolizumab (trade name Tecentriq®) was purchased from Roche. The method to generate HpLp (also known as KF025HpLp) can be found in US 2010/0203056 A1 (e.g., Example 10), in which the VH sequence of HpLp antibody was described in SEQ ID NO: 20 while the VL sequence was described in SEQ ID NO: 21.

The method to generate PCAB can be found in U.S. Pat. No. 7,943,743 B2 (e.g., Example 1), in which the VH sequence of the antibody was described in SEQ ID NO: 1 and the VL sequence was described in SEQ ID NO: 11.

2. Methods

To detect the binding affinity of 5C10H2L2, HpLp and PCAB to antigen PDL-1, antigen PDL-1 (5 μg/mL) was coated onto the surface of AR2G sensor by amino-coupling followed by blocking with ethanolamine. After equilibration in PBST, the binding between antigen captured on the biosensor and antibody was carried out, and the antibody was serially diluted with 3 fold dilution (initial concentration: 200 nM) with PBST (10 mM). The binding affinities of 5C10H2L2, HpLp and PCAB to antigen PDL-1 were analyzed by Fortebio Data Analysis 7.0.

3. Results

Figure 9:
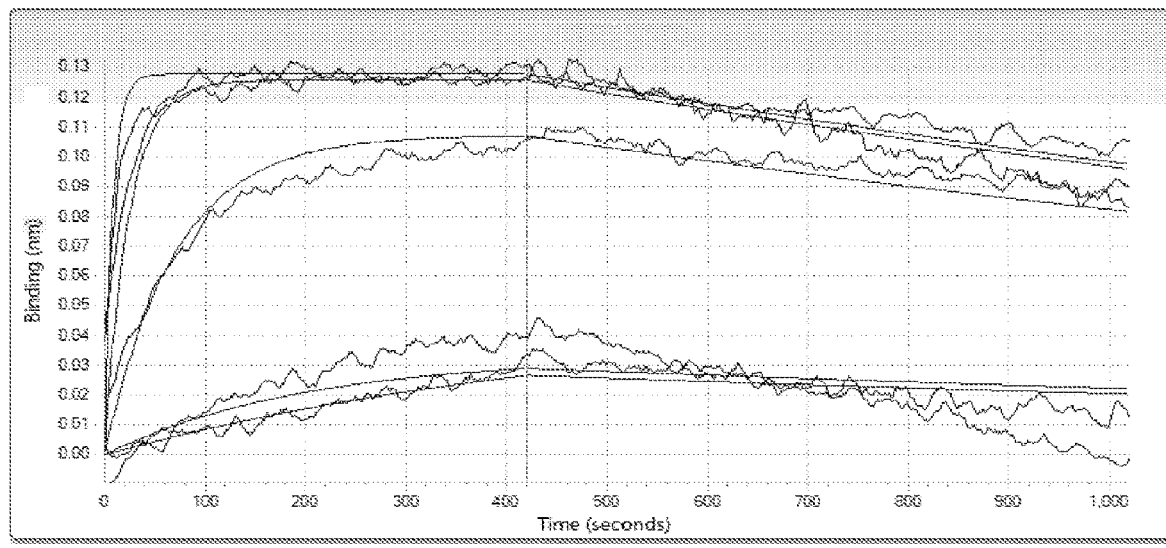
FIG. 9 Binding kinetics parameters of antibody 5C10H2L2 to PDL-1.
Figure 10:
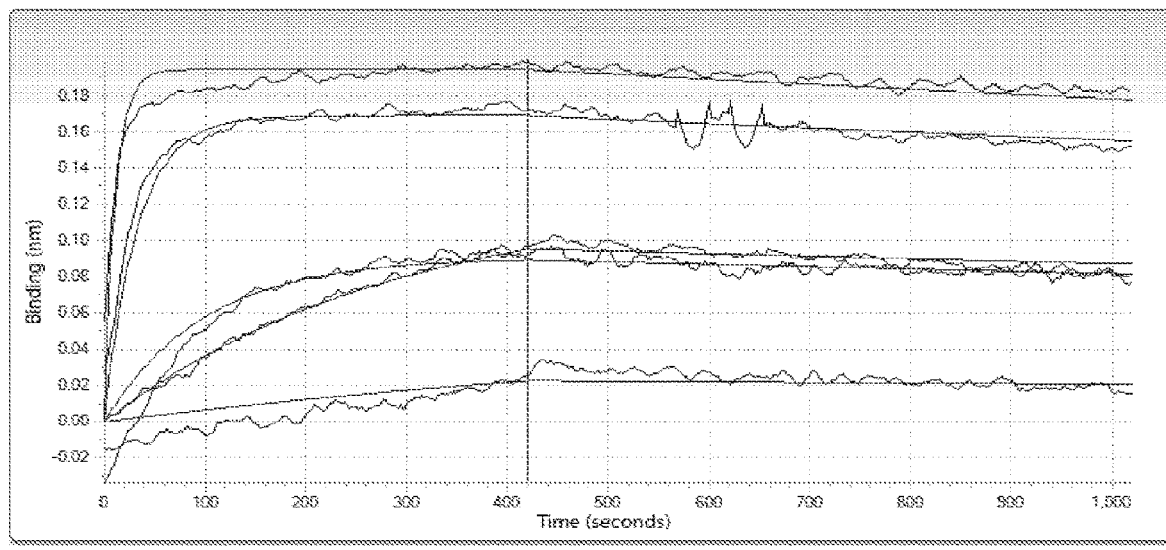
FIG. 10 Binding kinetics parameters of antibody HpLp to PDL-1.
Figure 11:
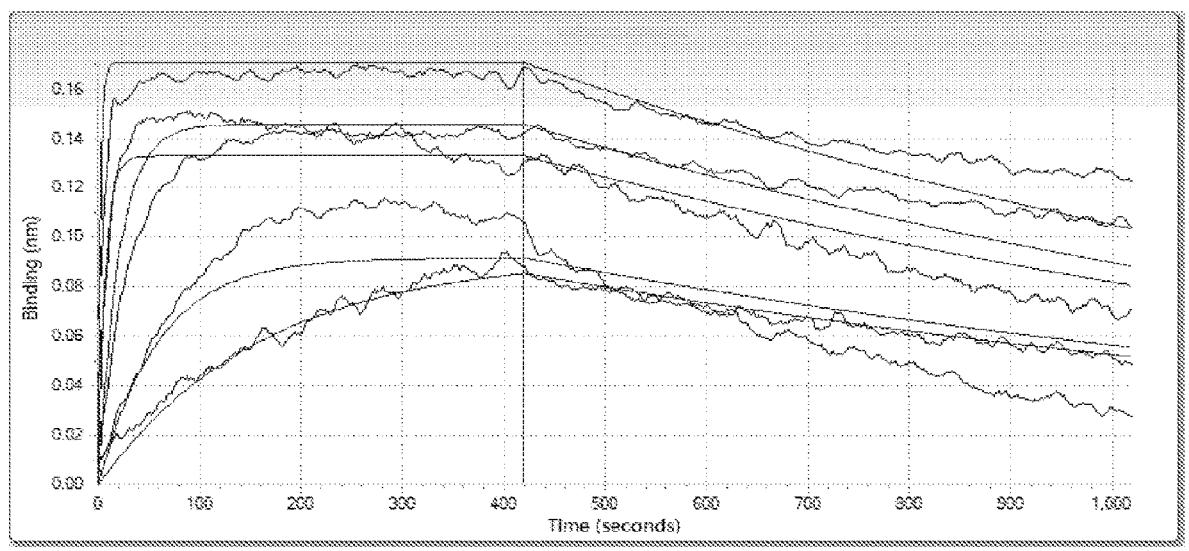
FIG. 11 Binding kinetics parameters of antibody PCAB to PDL-1.

Binding affinity and kinetic constants of 5C10H2L2, HpLp and PCAB to PDL-1 were shown in Table 2 and FIG. 9-11.

TABLE 2

Binding affinity and kinetic constants of 5C10H2L2, HpLp and PCAB to PDL-1

| Antibody | $K_D$ (M) | $K_{on}$(1/Ms) | SD ($K_{on}$) | $K_{dis}$(1/s) | SD ($K_{dis}$) |
|---|---|---|---|---|---|
| 5C10 H2L2 | 8.08E−11 | 5.58E+06 | 2.06E+05 | 4.51E−04 | 1.66E−05 |
| HpLp | 3.68E−11 | 4.07E+06 | 1.02E+05 | 1.50E−04 | 9.99E−06 |
| PCAB | 1.28E−10 | 6.55E+06 | 3.88E+05 | 8.37E−04 | 2.25E−05 |

$K_D$: Dissociation constant;
$K_{on}$: Association rate constant;
$K_{dis}$: dissociation rate constant;
$K_D = K_{dis}/K_{on}$.

The results showed that all the three antibodies bound to antigen with very high affinity. And the binding affinity of 5C10H2L2 and HpLp was higher than that of PCAB to antigen.

Example 6

Blocking PDL-1 From Interacting with PD-1 By Antibody 5C10, 5C10H2L2 and HpLp (Fortebio)

To detect the ability of 5C10, 5C10H2L2 and HpLp for blocking PDL-1 from interacting with PD-1, antigen PDL-1 (5 µg/mL) was coated onto the surface of AR2G sensor by amino-coupling followed by blocking with ethanolamine. After equilibration in PBST, the binding between antigen captured on the biosensor and antibody was carried out and the antibody was serially diluted with 3 fold dilution (initial concentration: 33.33 nM) with PBST (10 mM). The biosensor tips were then immersed in solution containing PD-1 protein (10 µg/ml) for 420 s.

Figure 12:
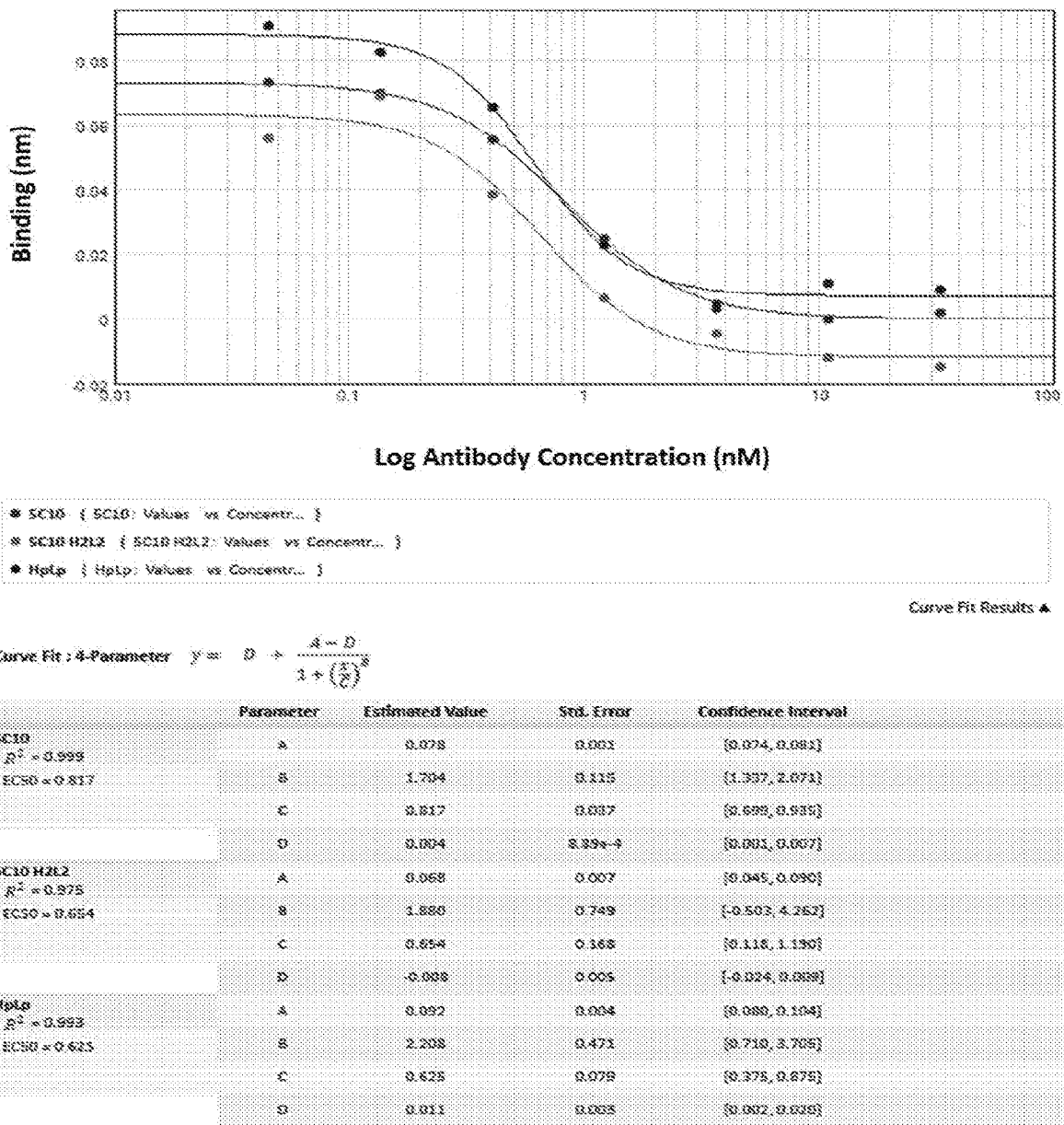
FIG. 12 Blocking PDL-1 from interacting with PD-1 by antibody 5C10, 5C10H2L2 and HpLp (Fortebio).
Figure 13:
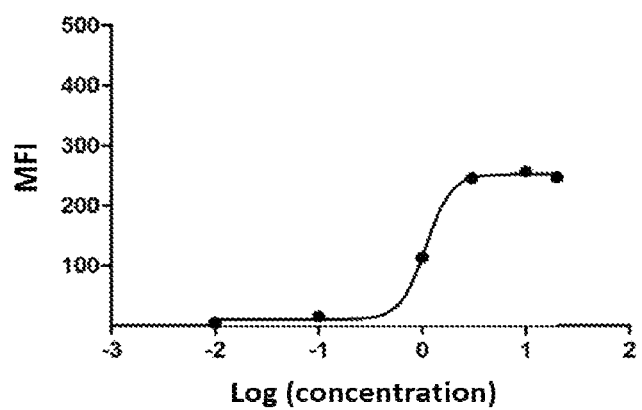
FIG. 13 Binding of 5C10H1L1 to PDL-1 positive 293T cells.
Figure 14:
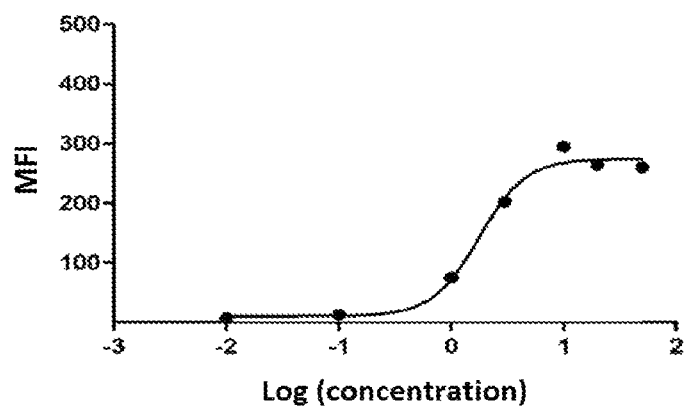
FIG. 14 Binding of 5C10H1L2 to PDL-1 positive 293T cells.
Figure 15:
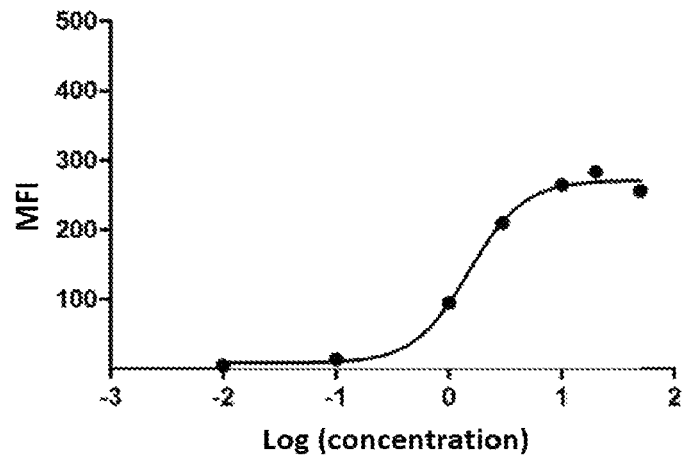
FIG. 15 Binding of 5C10H2L1 to PDL-1 positive 293T cells.
Figure 16:
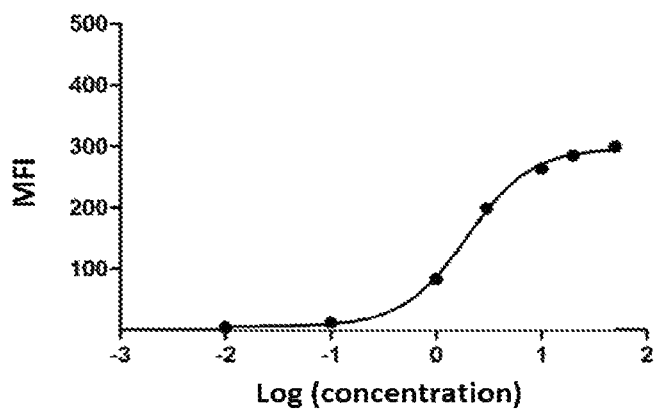
FIG. 16 Binding of 5C10H2L2 to PDL-1 positive 293T cells.
Figure 17:
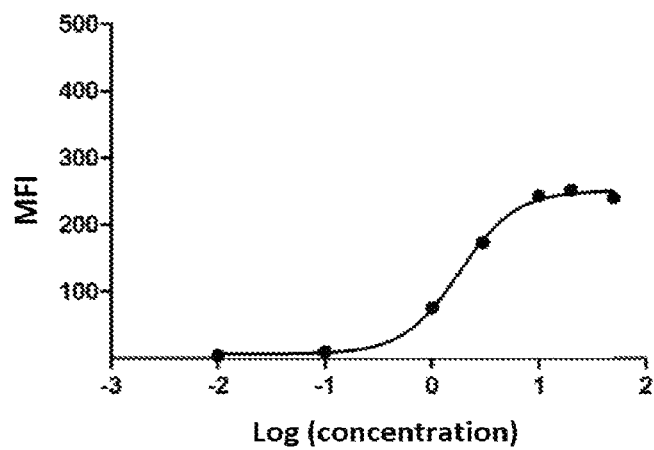
FIG. 17 Binding of HpLp to PDL-1 positive 293T cells.
Figure 18:
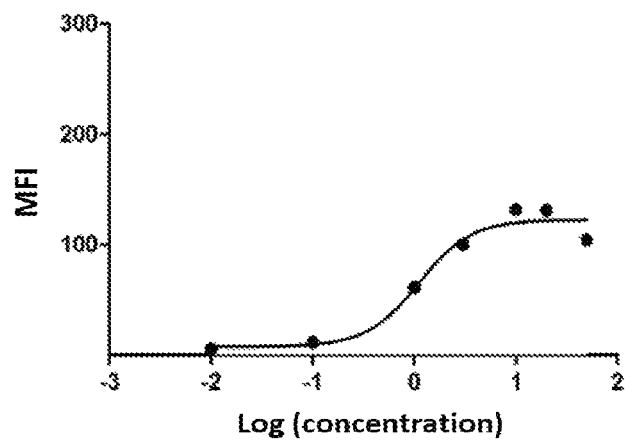
FIG. 18 Binding of PCAB to PDL-1 positive 293T cells.

As shown in FIG. 12, each antibody was able to effectively inhibit the binding of human PDL-1 to PD-1 in a dose-dependent manner, the fluorescence intensity of each dose and the fitted $EC_{50}$ were shown in Table 3.

TABLE 3

Blocking PDL-1 from interacting with PD-1 by antibody 5C10, 5C10H2L2 and HpLp

| Antibody (nM) | 5C10 | 5C10 H2L2 | HpLp |
|---|---|---|---|
| 33.33 | 0.0058 | −0.0109 | 0.0127 |
| 11.11 | 0.0038 | −0.0078 | 0.0149 |
| 3.704 | 0.0088 | −0.0007 | 0.0073 |
| 1.235 | 0.0289 | 0.0103 | 0.0268 |
| 0.4115 | 0.0599 | 0.0425 | 0.0697 |
| 0.1372 | 0.0739 | 0.0732 | 0.0867 |
| 0.04572 | 0.0773 | 0.0601 | 0.0947 |
| $EC_{50}$ (nM) | 0.817 | 0.654 | 0.625 |

The results show that all the three antibodies were able to effectively inhibit the binding of human PDL-1 to PD-1 in a dose-dependent manner.

Example 7

Blocking PDL-1 From Interacting with PD-1 By Antibody 5C10H2L2 and HpLp

The ability of 5C10H2L2 to block PD1/PDL-1 interaction was compared with HpLp by HTRF using the kit of PD1/PDL-1 binding assay (CISBIO; 63ADK000CPLPEH). The antibody 5C10H2L2 and HpLp were serially diluted with 3 fold dilution (initial concentration: 100 µg/mL; 10 gradients) with dilution buffer. 2 µl sample, 4 µl PDL-1-EuK and 4 µl Tag-PD1 were added to the solutions followed by transient centrifugation and incubation (20 min at room temperature). Then 10 µl anti-Tag-XL665 was further added to the solutions followed by transient centrifugation and incubation (2 hours at room temperature). Finally, the value was read by PHERA star Fs (BMG) and data was analyzed by Graph Prism.

The results showed that HpLp and 5C10H2L2 had similar ability to block the interaction of PD1/PDL-1 (67.29 ng/mL and 68.97 ng/mL respectively). Both antibodies could effectively inhibit the binding of human PDL-1 to PD-1.

Example 8

The Binding of Humanized Anti-PDL-1 Antibodies to Cells Expressing PDL-1 Determined By FACS Firstly 293T cells expressing PDL-1 were constructed, then the host cells were labeled by humanized antibodies 5C10H1L1, 5C10H1L2, 5C10H2L2, 5C10H2L1 and positive control antibodies (HpLp and PCAB). The specific binding of antibodies 5C10H1L1, 5C10H1L2, 5C10H2L2, 5C10H2L1 and positive control antibodies (HpLp and PCAB) to the antigen with natural conformation on the cell surface was analyzed by FACS.

Details are as follows:

1. Construction of 293T Cells Expressing PDL-1

The vector pLenti6.3-PDL-1 (Purchased from Invitrogen) containing PDL-1 was transfected into 293T cells according to manual of the lipofectamin transfection kit (purchased from Invitrogen). Cells stably expressing PDL-1 were obtained after screening.

2. Antibody Labeling and FACS Analysis 293T cells were collected after conventional trypsin treatment, and the number of cells per collection tube was $2\times10^5$. Each antibody dilution was prepared with PBS (1% BSA) at concentrations of 50 nM, 20 nM, 10 nM, 3 nM, 1 nM, 0.1 nM, 0.01 nM and 0 nM, respectively. Antibody dilutions were then incubated with 293 T cells expressing PDL-1 on ice for 2 hours followed by PBS washing for 3 times. FITC-Goat-Anti-Human IgG was diluted (1:100) with PBS and added to each tube for 100 µl, which was then incubated for 1 hour on ice. After 3 times PBS washing, the cells were resuspended by 300 µl PBS, and fluorescence signals were detected by FITC channels of flow cytometry.

3. Results

Binding of antibody 5C10H1L1, 5C10H1L2, 5C10H2L1, 5C10H2L2 and antibodies for positive control (HpLp and PCAB) to 293T cells expressing PDL-1 were shown in FIG. 13-18.

The results showed that all the antibodies could efficiently bind to the PDL-1 on the surface of 293T cell in a dose-dependent manner. After fluorescent quantitation analysis on the bound antibodies, the binding curves are fitted with standard model and binding efficacy $EC_{50}$ each antibody is calculated, as shown in Table 4.

TABLE 4

Fluorescence intensity analysis on antibody 5C10H1L1, 5C10H1L2, 5C10H2L2, 5C10H2L1, HpLp, PCAB binding to 293-T surface antigen PDL-1 by FACS

| Antibody/nM | \multicolumn{7}{c}{Mean Fluorescence Intensity (MFI)} | | | | | | | $EC_{50}$ (nM) |
|---|---|---|---|---|---|---|---|---|
| | 0.01 | 0.10 | 1.00 | 3.00 | 10.00 | 20.00 | 50.00 | |
| 5C10H1L1 | 4.84 | 15.27 | 113.99 | 245.65 | 256.56 | 247.63 | 194.04 | 1.084 |
| 5C10H1L2 | 7.25 | 12.63 | 74.81 | 202.24 | 294.53 | 264.22 | 260.09 | 1.771 |
| 5C10H2L2 | 4.85 | 12.92 | 83.59 | 199.45 | 263.95 | 285.02 | 299.63 | 1.962 |
| 5C10H2L1 | 4.64 | 13.54 | 94.70 | 209.32 | 264.17 | 283.13 | 255.58 | 1.504 |
| HpLp | 4.48 | 10.48 | 75.788 | 173.52 | 243.03 | 251.81 | 241.14 | 1.804 |
| PCAB | 5.55 | 11.82 | 61.12 | 99.86 | 131.66 | 130.95 | 104.43 | 1.108 |

The results showed that all the antibodies could efficiently bind to the target protein (PDL-1) on the surface of 293T cell in a dose-dependent manner.

Example 9

Determination of Binding Affinity of Humanized Anti-PDL-1 Antibodies to PDL-1 By Indirect ELISA Indirect enzyme-linked immunosorbent assay (ELISA) was performed to evaluate the binding affinity of 5C10H1L1, 5C10H1L2, 5C10H2L2, 5C10H2L1, and positive controls antibodies (HpLp and PCAB) to human PDL-1. ELISA plate was coated with human PDL-land incubated at 4° C. overnight, followed by blocking with 1% BSA at 37° C. for 2 hours. Antibodies were then added to each well and incubated at 37° C. for 30 minutes. A secondary antibody, HRP conjugated goat anti-human IgG (H+L) (Jackson, 109-035-088) was added. TMB substrate (Neogen, 308177) was added for chromogenic reaction and was incubated for 5 minutes. Absorbance was read at 450 nm.

Figure 19:
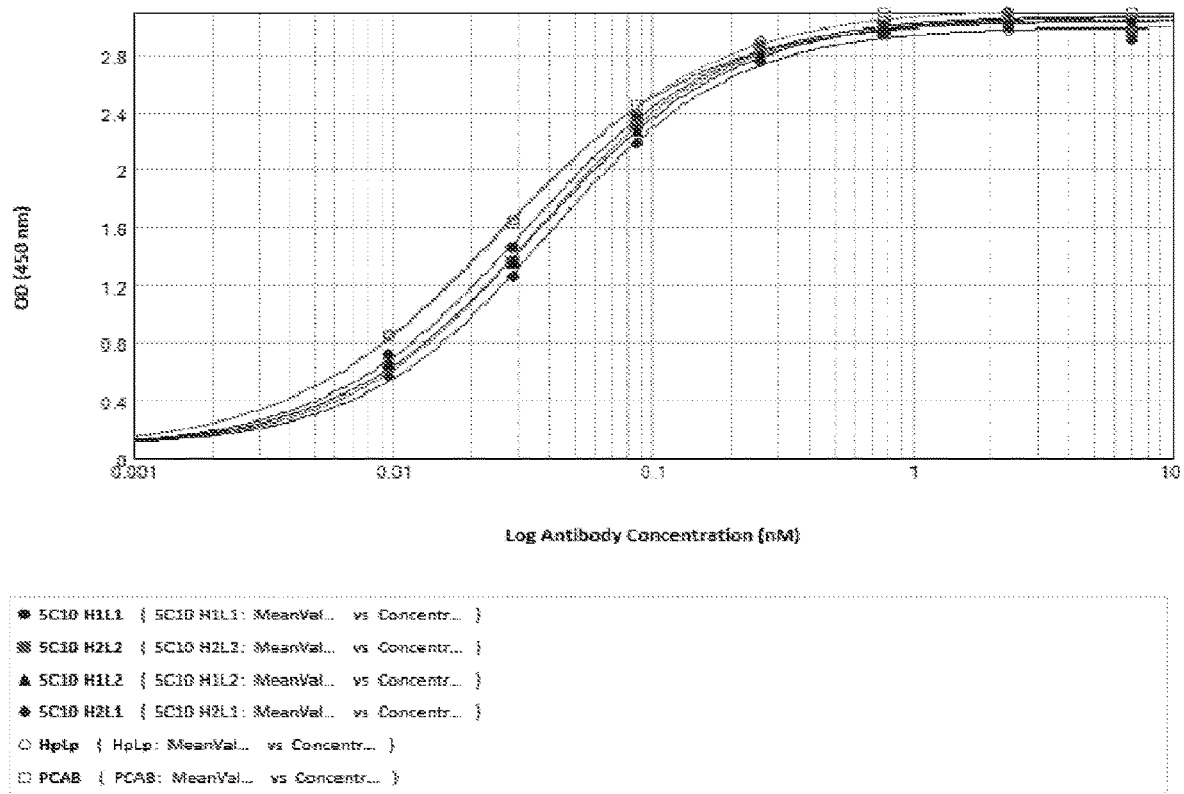
FIG. 19 Binding of 5C10H1L1, 5C10H1L2, 5C10H2L2 or 5C10H2L1 to human PDL-1 recombinant protein by indirect ELISA.

The results are shown in FIG. 19. As the figure indicates, 5C10H1L1, 5C10H1L2, 5C10H2L2, 5C10H2L1, HpLp, and PCAB can effectively bind to human PDL-1 in a dose-dependent manner. The fluorescent intensity of each dosage and calculated binding efficiency represented by $EC_{50}$ after curve fitting are listed in Table 5.

The results showed that the antibodies of the invention could effectively bind to the human PDL-1 in a dose-dependent manner.

Example 10

Binding Affinity of Antibody 5C10H2L2 to Monkey PDL-1 By Indirect ELISA

In consideration of pharmacokinetics and toxicology experiments to be conducted on experiment animals, the purpose of this experiment is to determine whether antibody 5C10H2L2 can bind to monkey PDL-1; if antibody 5C10H2L2 can bind to monkey PDL-1, then monkey can be used for pharmacokinetics and toxicology experiments.

The binding of 5C10H2L2 and positive control HpLp to monkey PDL-1 were measured by indirect ELISA. ELISA plate was coated with monkey PDL-1 and incubated at 4° C. overnight followed by blocking with 1% BSA in PBS at 37° C. for 2 hours. Antibodies were then added to each well and incubated at 37° C. for 30 minutes. A secondary antibody, HRP conjugated goat anti-human IgG (H+L) (Jackson, 109-035-088) was added. TMB substrate (Neogen, 308177) was added for chromogenic reaction and was incubated for 5 minutes. Absorbance was read at 450 nm.

Figure 20:
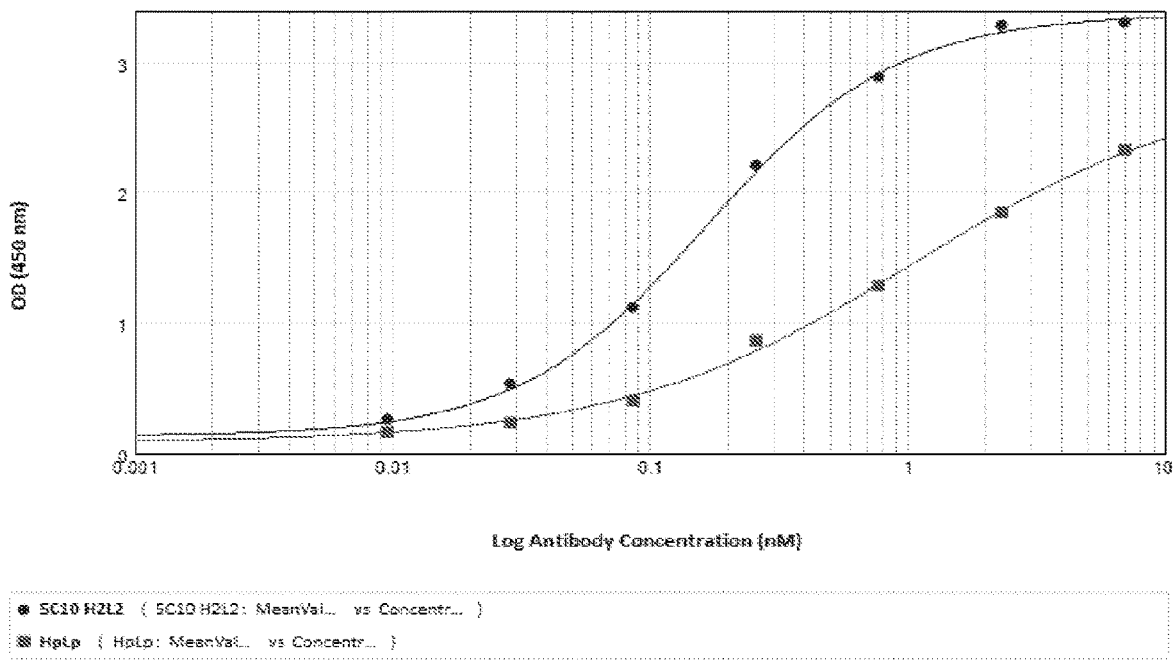
FIG. 20 Binding of 5C10H2L2 or HpLp to monkey PDL-1 recombinant protein by indirect ELISA.

The results of binding activity of 5C10H2L2 and HpLp to monkey PDL-1 are shown in FIG. 20. As is shown in FIG. 20, 5C10H2L2 and HpLp can effectively bind to monkey PDL-1 in a dose-dependent manner. The fluorescent intensity of each dosage and calculated binding efficiency represented by $EC_{50}$ after curve fitting are shown in Table 6.

TABLE 5

Binding of antibody 5C10H1L1, 5C10H1L2, 5C10H2L2, 5C10H2L1, HpLp and PCAB to human PDL-1 (indirect ELISA)

Antigen coated: PDL-1-mFc (1 µg/ml)

| Antibody (µg/ml) | 5C10 H1L1 | | 5C10 H2L2 | | 5C10 H1L2 | | 5C10 H2L1 | | HpLp | | PCAB | |
|---|---|---|---|---|---|---|---|---|---|---|---|---|
| 1.000 | 3.168 | 2.923 | 2.914 | 3.010 | 3.075 | 2.983 | 2.839 | 2.985 | 3.023 | 2.934 | 3.017 | 3.177 |
| 0.333 | 3.153 | 3.044 | 3.176 | 2.974 | 2.992 | 3.089 | 3.004 | 2.997 | 2.854 | 3.099 | 3.006 | 3.158 |
| 0.111 | 2.958 | 2.926 | 3.084 | 2.899 | 3.006 | 2.999 | 3.001 | 2.921 | 2.995 | 3.085 | 3.037 | 3.163 |
| 0.037 | 2.950 | 2.786 | 2.930 | 2.758 | 2.783 | 2.827 | 2.814 | 2.704 | 2.908 | 2.894 | 2.843 | 2.892 |
| 0.012 | 2.495 | 2.228 | 2.337 | 2.280 | 2.243 | 2.305 | 2.169 | 2.202 | 2.446 | 2.315 | 2.374 | 2.525 |
| 0.004 | 1.574 | 1.336 | 1.367 | 1.346 | 1.320 | 1.408 | 1.309 | 1.205 | 1.673 | 1.643 | 1.502 | 1.770 |
| 0.001 | 0.816 | 0.616 | 0.659 | 0.622 | 0.624 | 0.690 | 0.595 | 0.560 | 0.866 | 0.855 | 0.746 | 0.940 |
| 0.000 | 0.053 | 0.055 | 0.059 | 0.052 | 0.052 | 0.054 | 0.054 | 0.055 | 0.053 | 0.059 | 0.055 | 0.055 |
| 2ND | \multicolumn{12}{c}{HRP conjugated goat anti-human IgG as a secondary antibody} |
| $EC_{50}$ (nM) | 0.032 | | 0.035 | | 0.035 | | 0.038 | | 0.025 | | 0.027 | |

TABLE 6

Binding of antibody 5C10H2L2 and HpLp to monkey PDL-1 (indirect ELISA)

| Antibody dilution (µg/ml) | Antigen coated: monkey PDL-1-his (1 µg/ml) | | | |
|---|---|---|---|---|
| | 5C10 H2L2 | | HpLp | |
| 1.000 | 3.328 | 3.302 | 2.531 | 2.123 |
| 0.333 | 3.395 | 3.169 | 1.969 | 1.740 |
| 0.111 | 3.040 | 2.740 | 1.424 | 1.151 |
| 0.037 | 2.411 | 2.013 | 0.969 | 0.763 |
| 0.012 | 1.194 | 1.047 | 0.431 | 0.374 |
| 0.004 | 0.562 | 0.495 | 0.243 | 0.221 |
| 0.001 | 0.267 | 0.244 | 0.171 | 0.153 |
| 0.000 | 0.110 | 0.115 | 0.111 | 0.104 |
| HRP conjugated goat anti-human IgG as a secondary antibody | | | | |
| $EC_{50}$ (nM) | 0.165 | | 1.049 | |

The results showed that both antibody 5C10H2L2 and HpLp could effectively bind to monkey PDL-1 in a dose-dependent manner, and the binding capacity of 5C10H2L2 is higher than that of HpLp.

Example 11

Binding of 5C10H2L2 to Human PDL-1, Human PD-L2 and Mouse PDL-1 By Indirect ELISA The binding of 5C10H2L2 to human PDL-1, human PD-L2 (Sino Biological Inc., Cat. 10292-H08H) and mouse PDL-1 (Sino Biological Inc., Cat. 50010-M08H) was analyzed by indirect ELISA. Human PDL-1, human PD-L2, or mouse PDL-1 was added in ELISA plate at 0.5 µg/ml with 100 µl per well individually, and incubated at 4° C. overnight. Antibodies were serially diluted starting from 1 µg/ml (3 fold dilution; 11 gradients). Wells were blocked with 1% BSA at 37° C. for 2 hours. A Secondary antibody, HRP conjugated goat anti-human IgG (H-FL) (Jackson, 109-035-088), was added at 1:20000 dilution. TMB substrate (Neogen, 308177) was added for chromogenic reaction and was incubated for 5 minutes. Absorbance was read at 450 nm.

Figure 21:
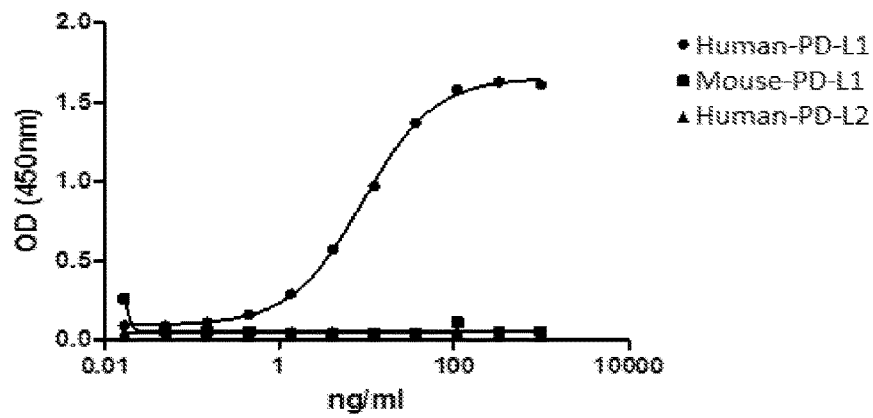
FIG. 21 Binding of 5C10H2L2 to human PDL-1, human PDL-2 or mouse PDL-1 recombinant protein by ELISA.

The results of 5C10H2L2 binding to human PDL-1, human PD-L2 and mouse PDL-1 are shown in FIG. 21. As is shown in FIG. 21, 5C10H2L2 can effectively bind to human PDL-1 in a dose-dependent manner. The fluorescent intensity of each dosage and calculated binding efficiency after curve fitting $EC_{50}$=9.16 ng/ml, while it does not bind to human PD-L2 and mouse PDL-1.

In conclusion, 5C10H2L2 can specifically combine to human PDL-1 while Atezolizumab can bind to mouse PDL-1 (Tecentriq® PHARMACOLOGY REVIEW, FDA, Application number 761034Orig1s000). These data indicates that 5C10H2L2 antibody has excellent specificity.

Example 12

Determination of Competitive Binding Activity of Humanized Antibodies for PDL-1 with PD-1 By Competitive ELISA Competitive ELISA was performed to evaluate the ability of 5C10H1L1, 5C10H1L2, 5C10H2L2, 5C10H2L1, and positive controls (HpLp and PCAB) competing with PD-1 in binding to human PDL-1. ELISA plate was coated with receptor and incubated at 4° C. overnight. Wells were blocked with 1% BSA at 37° C. for 2 hours. After that, antibody and PDL-1-mFc were mixed and incubated at room temperature for 15 minutes which was then subsequently added to each well and incubated at 37° C. for 30 minutes. A secondary antibody, HRP conjugated goat anti-mouse IgG (H+L) (Jackson, 109-035-062) was added. TMB substrate (Neogen, 308177) was added for chromogenic reaction and was incubated for 5 minutes. Absorbance was read at 450 nm.

Figure 22:
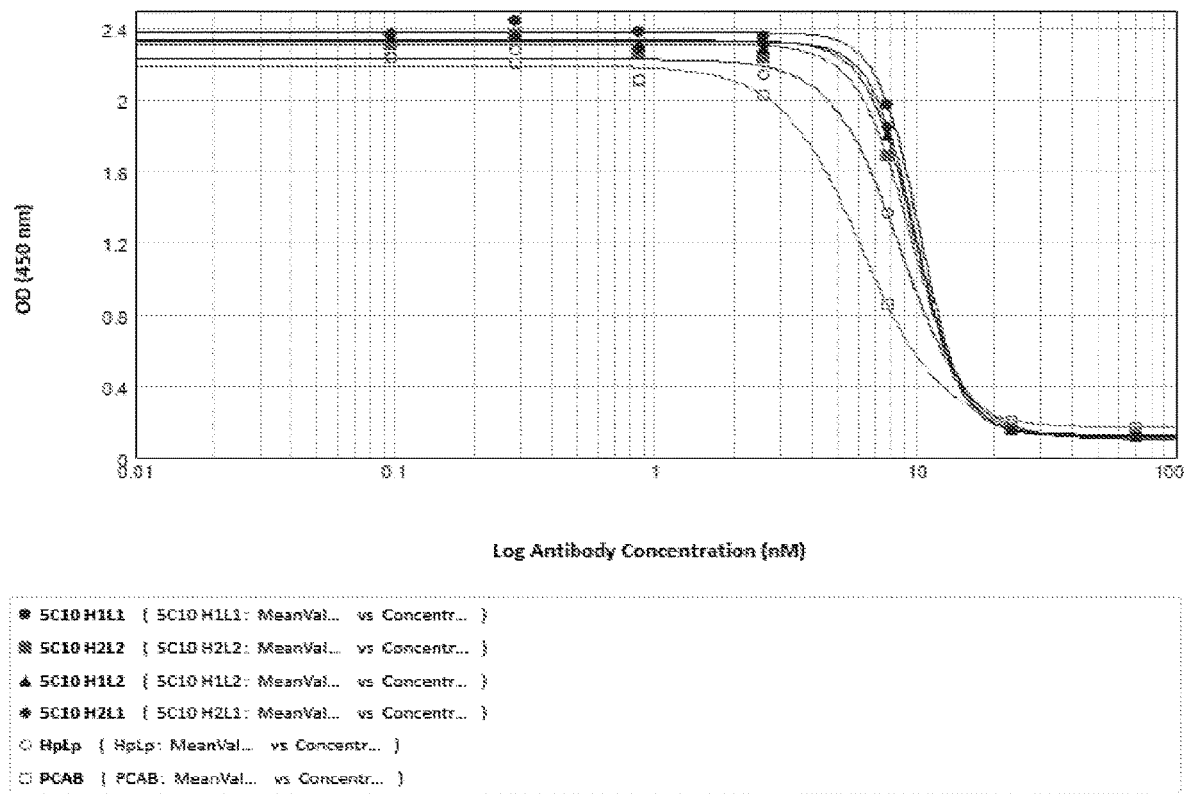

The results of the binding activity of these antibodies to PDL-1 are shown in FIG. 22. It can be seen that 5C10H1L1, 5C10H1L2, 5C10H2L2, 5C10H2L1, HpLp and PCAB can compete with PD-1 in binding to PDL-1 in a dose-dependent manner. The fluorescent intensity of each dosage and calculated binding efficiency represented by $EC_{50}$ after curve fitting are shown in Table 7.

TABLE 7

Competitive Binding of antibody 5C10H1L1, 5C10H1L2, 5C10H2L2, 5C10H2L1, HpLp and PCAB to PDL-1 (competitive ELISA)

Antigen coated: PD-1-hFc 0.5 µg/ml

| Antibody (µg/ml) | 5C10 H1L1 | | 5C10 H2L2 | | 5C10 H1L2 | | 5C10 H2L1 | | KF025 HPLP (HpLp) | | PCAB | |
|---|---|---|---|---|---|---|---|---|---|---|---|---|
| 10 | 0.131 | 0.123 | 0.124 | 0.124 | 0.123 | 0.117 | 0.138 | 0.124 | 0.130 | 0.127 | 0.175 | 0.176 |
| 3.3333 | 0.155 | 0.153 | 0.153 | 0.165 | 0.151 | 0.157 | 0.158 | 0.159 | 0.152 | 0.162 | 0.199 | 0.215 |
| 1.1111 | 1.961 | 1.999 | 1.672 | 1.695 | 1.797 | 1.799 | 1.843 | 1.871 | 1.501 | 1.244 | 0.806 | 0.905 |
| 0.3704 | 2.383 | 2.331 | 2.238 | 2.251 | 2.292 | 2.292 | 2.230 | 2.407 | 2.180 | 2.106 | 2.152 | 1.911 |
| 0.1235 | 2.399 | 2.367 | 2.241 | 2.291 | 2.289 | 2.328 | 2.326 | 2.256 | 2.120 | 2.022 | 2.146 | 2.078 |
| 0.0412 | 2.430 | 2.456 | 2.314 | 2.413 | 2.338 | 2.364 | 2.358 | 2.350 | 2.358 | 2.208 | 2.267 | 2.136 |
| 0.0137 | 2.395 | 2.334 | 2.298 | 2.331 | 2.339 | 2.368 | 2.394 | 2.357 | 2.186 | 2.297 | 2.290 | 2.199 |
| 0.0000 | 2.345 | 2.343 | 2.372 | 2.368 | 2.345 | 2.369 | 2.311 | 2.276 | 2.329 | 2.298 | 2.116 | 2.262 |
| PDL-1-mFc: 1 µg/ml | | | | | | | | | | | | |
| HRP conjugated goat anti-mouse IgG as a secondary antibody | | | | | | | | | | | | |
| $EC_{50}$ | 10.37 | | 9.683 | | 9.952 | | 10.03 | | 8.73 | | 6.145 | |

The results showed that all the antibodies detected could competitively and effectively bind to the antigen PDL-1 in a dose-dependent manner.

Example 13

Determination of Competitive Binding Activity of Antibody 5C10H2L2 for PDL-1 with B7-1 By Competitive ELISA The ability of 5C10H2L2 and positive control antibody (HpLp and PCAB) to compete for PDL-1 binding with B7-1 (B7-1-hFc, obtained by Preparation Example 3) was determined by competitive ELISA. ELISA plate was coated with PDL-1 and incubated at 4° C. overnight. Wells were blocked with 1% BSA at 37° C. for 2 hours. After that, antibody and PDL-1-mFc were mixed and incubated at room temperature for 15 minutes which was then subsequently added to each well and incubated at 37° C. for 30 minutes. A secondary antibody, HRP conjugated goat anti-mouse IgG (H+L) (Jackson, 109-035-062) was added. TMB substrate (Neogen, 308177) was added for chromogenic reaction and was incubated for 5 minutes. Absorbance was read at 450 nm.

Figure 23:
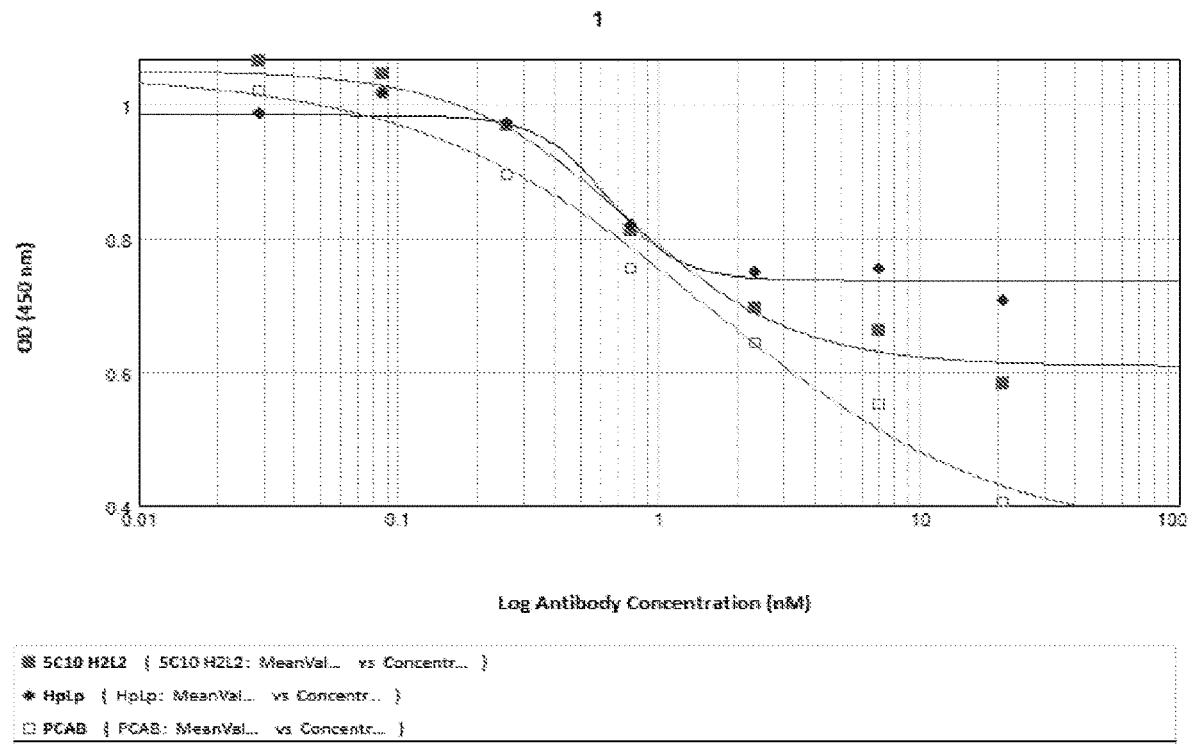

The results of the competition of 5C10H2L2 for binding PDL-1 with B7-1 are shown in FIG. 23 that 5C10H2L2, HpLp and PCAB can effectively compete with B7-1 for binding PDL-1. the fluorescent intensity of each dosage and calculated binding efficiency represented by $EC_{50}$ after curve fitting are shown in Table 8.

TABLE 8

Competitive ELISA results of antibody 5C10H2L2, HpLp, PCAB and B7-1 in competitive binding to PDL-1

| | Antigen coated: PDL-1-mFc (1 µg/ml) | | | | | |
|---|---|---|---|---|---|---|
| Antibody (µg/ml) | 5C10 H2L2 | | HpLp | | PCAB | |
| 3 µg/ml | 0.583 | 0.583 | 0.735 | 0.683 | 0.400 | 0.413 |
| 1:3 | 0.661 | 0.665 | 0.731 | 0.781 | 0.525 | 0.581 |
| 1:9 | 0.694 | 0.699 | 0.713 | 0.789 | 0.606 | 0.682 |
| 1:27 | 0.798 | 0.824 | 0.791 | 0.853 | 0.762 | 0.747 |
| 1:81 | 0.965 | 0.976 | 0.988 | 0.959 | 0.889 | 0.906 |
| 1:243 | 1.043 | 1.052 | 0.985 | 1.055 | 1.031 | 1.009 |
| 1:729 | 1.064 | 1.069 | 0.990 | 0.986 | 1.029 | 1.013 |
| 0.000 | 1.052 | 0.984 | 0.955 | 0.938 | 1.013 | 1.036 |
| | B7-1-hFc-bio: 0.4 µg/ml | | | | | |
| Secondary antibody | Horseradish peroxidase labeled streptavidin (SA-HRP) (1:4000) | | | | | |
| $EC_{50}$(nM) | 0.756 | | 0.639 (Incomplete competition*) | | 1.554 | |

*Incomplete competition. It should be noted that the data window of HpLp in the competitive binding experiment is smaller than the other two antibodies. As shown in Table 7, the decrease of OD is not obvious with the increasing of HpLp concentration starting from 1:27 dilution (such as 1:9, 1:3, 3 µg/ml).

The results indicate that all the antibodies determined can compete with B7-1 for binding PDL-1, in which the competitive binding activity of 5C10H2L2 is stronger than that of PCAB, and the $EC_{50}$ of 5C10H2L2 is about half of that of PCAB. The competitive binding activity of HpLp does not increase significantly as its concentration increasing.

Example 14

Cell Biological Activity Analysis of 5C10H2L2 and Positive Control Antibodies (HpLp and PCAB)

To investigate the effects of monoclonal antibody 5C10H2L2 and positive control (HpLp and PCAB) on the secretion of IL-2 and IFN-γ in peripheral blood mononuclear cells (PBMCs), Ficoll-Paque Plus (GE Healthcare LOT No. 171440-02) was used for PBMC isolation. IL-4 (Peprotech K2513, 1000 U/ml) and GM-CSF (Peprotech H1513, 1000 U/ml) were added to the PBMCs for induction of 6 days. After that, TNF-α (Peprotech G1513, 200 U/ml) was further added to the PBMCs and cells for induction of 3 days to obtain DC cells.

T cells was isolated from PBMCs. DC cells were mixed and cultured with T cells at a ratio of 1:10. After 5-6 days of incubation with different concentrations of antibody 5C10H2L2 (hIgG as control), ELISA was carried out to evaluate the secretion of IFN-γ (kit purchased from Dakewe Biotech Inc.) and IL-2 (kit purchased from Dakewe Biotech Inc.).

Figure 24:
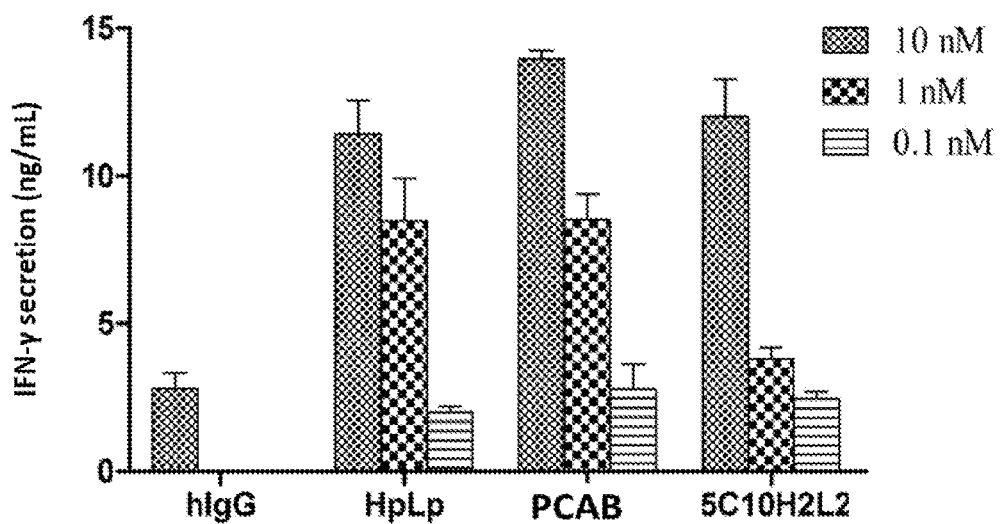
Figure 25:
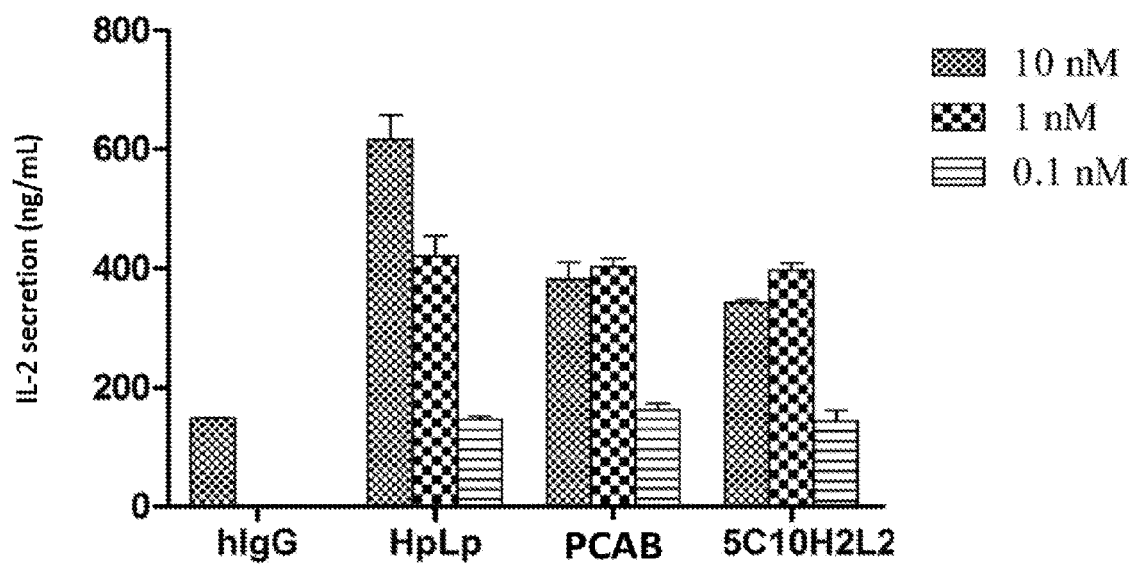

Secretion results of IFN-γ and IL-2 from DC and T cell mixture were shown in FIG. 24 and FIG. 25, respectively. The results show that 5C10H2L2, HpLp and PCAB could effectively induce the secretion of IFN-γ and IL-2 in a dose-dependent manner.

Example 15

Design and Preparation of Monoclonal Antibody 5C10H2L2-IgG1mt with Modified IgG1 Constant Region In the present invention, the heavy chain constant region is Ig gamma-1 chain C region, ACCESSION: P01857; the light chain constant region is Ig kappa chain C region, ACCESSION: P01834. The amino acids at 234, 235 and 237 sites by EU-number system were mutated as follows: L234A, L235A and G237A. The mutant antibody was named as 5C10H2L2-IgG1mt, which was prepared by the method of Example 4.

Example 16

Dynamic Affinity of 5C10H2L2-IgG1mt to FcγRIIIa and C1q Determined By ForteBio 1. The affinity and binding kinetics of 5C10H2L2-IgG1mt, Tecentriq® to FcγRIIIa were characterized by ForteBio (purchased from Pall Cat. No. Octet, Qke) as follows:

The purified FcγRIIIa-Biotin was coupled to streptavidin-coated SA chip through biotin-streptavidin binding using standard methods and kits provided by ForteBio with fixed conditions (1 μg/ml FcγRIIIa-Biotin, 300 seconds). The chip was bound by antibody at concentration of 4000 nM for 120 seconds followed by incubation in PBST (pH7.4) for 180 seconds for dissociation. The binding and dissociation curve were analyzed by Octet software.

Figure 26A:
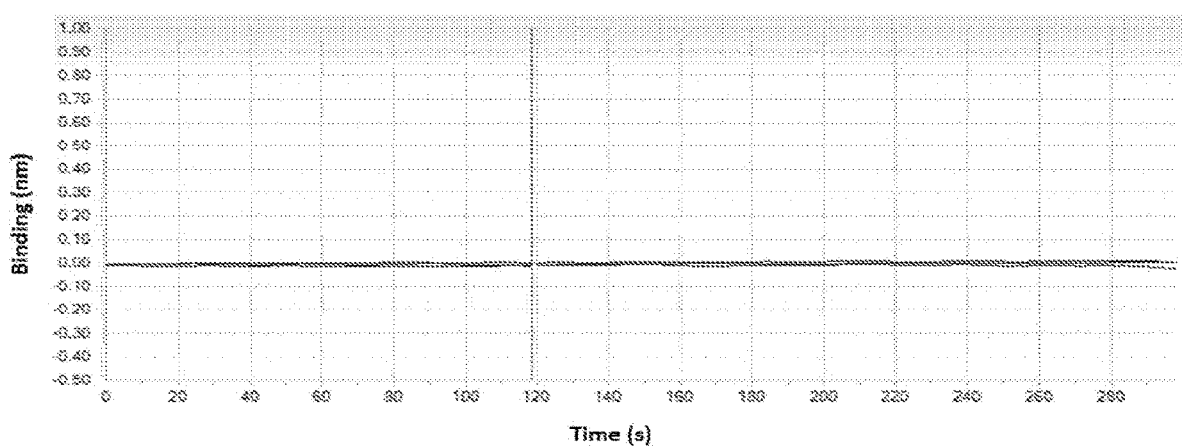
FIG. 26A Binding affinity and kinetic constants of 5C10H2L2-IgG1mt to FcγRIIIa by Biacorc.
Figure 26B:
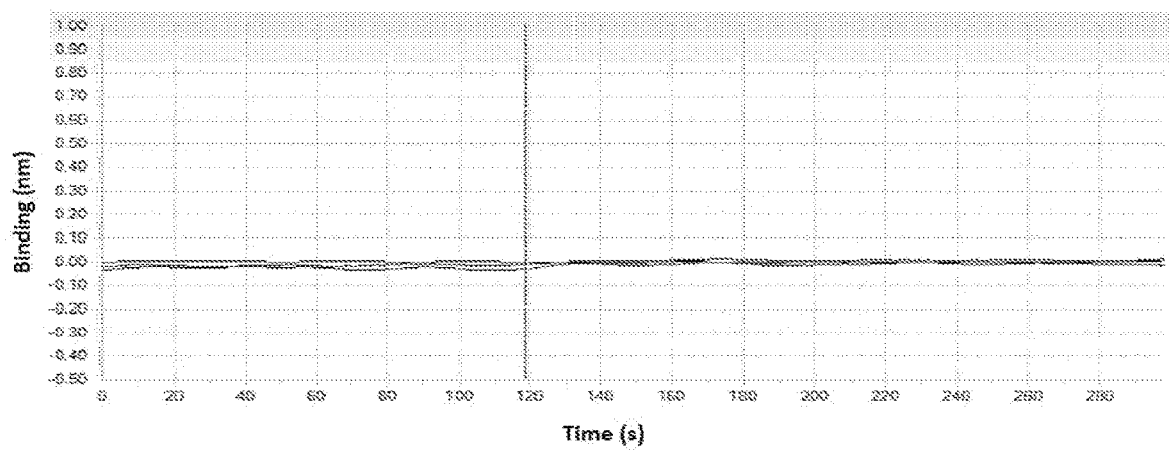
FIG. 26B Binding affinity and kinetic constants of Tecentriq® to FcγRIIIa by Biacore.

The results are shown in FIGS. 26A and 26B, that 5C10H2L2-IgG1mt and Tecentriq® did not bind to FcγRIIIa, which indicated that both of them do not have ADCC activity.

Figure 27A:
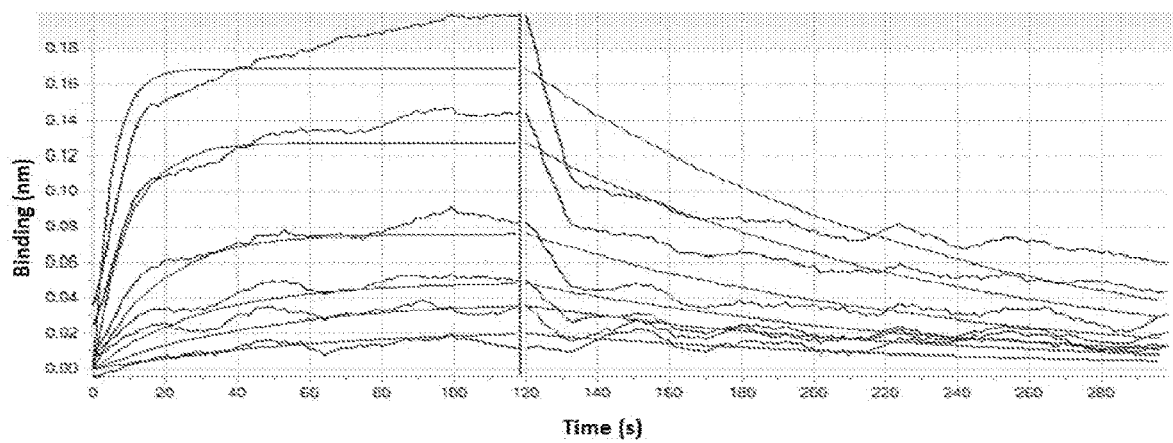
FIG. 27A Binding affinity and kinetic constants of 5C10H2L2-IgG1mt to C1q by Biacore.
Figure 27B:
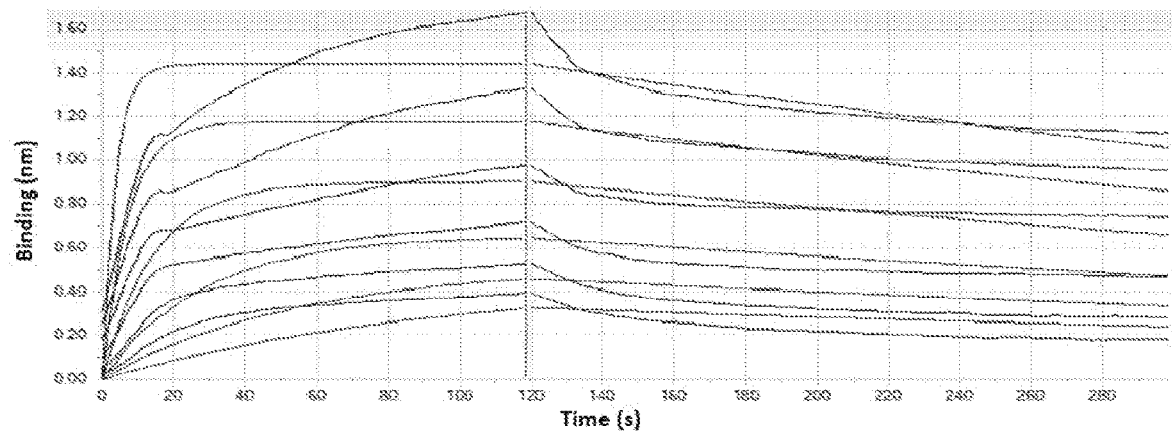
FIG. 27B Binding affinity and kinetic constants of Tecentriq® to C1q by Biacore.

2. The affinity and binding kinetics of 5C10H2L2-IgG1mt, Tecentriq® to C1q (purchased from Fitzgerald, Cat. No. 32R-AC049) were characterized by ForteBio as follows:

The purified antibody was coupled to streptavidin-coated SA chip through biotin-streptavidin binding using standard methods and kits provided by ForteBio with fixed conditions (20 μg/ml Antibody-Biotin, 300 seconds). The chip was then bound by C1q at concentration of 200 nM (2 fold dilution) for 120 seconds followed by incubation in PBST (pH7.4) for 180 seconds for dissociation. The binding and dissociation curve were analyzed by Octet software. In order to minimize the effect of the affinity on the binding constant estimation, only the data segment corresponding to the beginning of binding and dissociation phases was fitted. The values of $K_D$, $K_{on}$ and $K_{off}$ are shown in Table 9, and curves are shown in FIGS. 27A and 27B.

TABLE 9

Dynamic Affinity of 5C10H2L2-IgG1mt and Tecentriq® to C1q

| Antibody | $K_D$ (M) | $K_{on}$ (1/Ms) | $K_{dis}$ (1/s) |
|---|---|---|---|
| 5C10H2L2-IgG1mt | 8.53E−09 | 9.86E+05 | 8.41E−03 |
| Tecentriq® | 1.30E−09 | 1.36E+06 | 1.76E−03 |

The results demonstrates that 5C10H2L2-IgG1mt has a lower dynamic affinity than Tecentriq® to C1q.

Example 17

CDC Activity of 5C10H2L2-IgG1mt

The PDL-1 positive tumor cells HCC1954 (purchased from ATCC Cat. No. CRL-2338) were cultured with the corresponding medium (RPMI1640+10% bovine serum). And 5C10H2L2-IgG1mt was serially diluted with medium (RPMI1640+10% human serum) starting at 10000 μg/mL (5 fold dilution for 10 gradients). The above-mentioned tumor cells were treated with trypsin and a several tubes of cells were collected and resuspended in the corresponding medium (RPMI1640+10% human serum) and then added to the 96-well plate (10000 cells/well) with different dilutions of antibodies for 5 hours incubation. After that, 20 μl of CCK8 reagent (purchased from Dongren Chemical Technology Co., Ltd., Cat. No. CK04, Lot: JJ744) was added to each well for 3 hours incubation. The absorbance was read at 450 nm by microplate reader (Molecular Devices, Model: SpectraMax M2). The activity of the dehydrogenase within the mitochondria reflects the cytotoxicity of the antibody to HCC1954 cells.

The results demonstrate that 5C10H2L2-IgG1mt does not have CDC effect on HCC1954 cells.

Example 18

In Vivo Tumor Inhibition Effects on Colon Cancer

1. Samples

5C10H2L2-IgG1mt, Tecentriq® and human IgG were provided by Sichuan Kelun Pharmaceutical Research Institute Co. Ltd. Tecentriq® was purchased from Roche, and human IgG was purchased from Chengdu Rongsheng Pharmaceutical Co., Ltd.

Preparation: three samples are diluted with saline containing 0.1% BSA to desired concentrations.

Cells and Animals

MC-38/H-11 cells were derived from mouse colon cancer MC-38 Cells (purchased from Cobioer, Cat. CBP60825) whose endogenous mouse PDL-1 was knocked out by CRISPR/Cas9, and human PDL-1 was transfected into the cells. Thus, MC-38/H-11 cells would only express human PDL-1 protein.

C57BL/6 mice, 7-8 weeks old, female, were purchased from Shanghai Slac Laboratory Animal Co., Ltd.

2. Procedure

Each mouse was subcutaneously inoculated with $1 \times 10^5$ MC-38/H-11 cells and randomly grouped to receive intraperitoneal injection (IP) of samples once every other day (Q2D) from the second day of tumor inoculation (DO). The injection doses were as follows: human IgG (15 mg/kg), 5C10H2L2-IgG1mt (1.5, 5, 15 mg/kg) and Tecentriq® (15 mg/kg). Each group had 10 mice with injection volume of 0.1 mL/10 g body weight.

3. Experimental Indicators

Impact of the drugs on tumor growth is indicated by T/C % or tumor growth inhibition (TGI) (%).

The tumor diameter was measured twice a week with a vernier caliper. The tumor volume (V) was calculated as:

$V = 1/2 \times a \times b^2$, where a and b represent length and width, respectively.

T/C % = T/C×100, where C represents the tumor volume or tumor weight of control group, and T represents the tumor volume or tumor weight of the treatment group.

Tumor growth inhibition (TGI) (%)=(C−T)/C×100, where C represents the tumor volume or tumor weight of control group, and T represents the tumor volume or tumor weight of the treatment group. 4. Results As shown in Table 10 below.

TABLE 10

Efficacy of 5C10H2L2-IgG1mt (1.5 mg/kg, 5 mg/kg, and 15 mg/kg) and Tecentriq® to subcutaneous xenografts of colon cancer to MC-38/H-11

| Group/Dosage | Average tumor volume (mm³) D 27 | T/C (%) D 27 | Tumor growth inhibition rate TGI (%) | Median tumor volume (mm³) D 27 | Tumor growth inhibition rate TGI (%) | Median tumor weight (g) D 27 | Tumor growth inhibition rate TGI (%) | Tumor formation rate (%) |
|---|---|---|---|---|---|---|---|---|
| Human IgG (15 mg/kg) | 2486.0 | — | — | 2126.7 | — | 25.0 | — | 100.0 |
| 5C10H2L2-IgG1mt (1.5 mg/kg) | 898.5 | 36.1 | 63.9 | 0.0 | 100.0 | 0.0 | 100.0 | 40.0 |

TABLE 10-continued

Efficacy of 5C10H2L2-IgG1mt (1.5 mg/kg, 5 mg/kg, and 15 mg/kg) and Tecentriq ® to subcutaneous xenografts of colon cancer to MC-38/H-11

| Group/Dosage | Average tumor volume (mm³) D 27 | T/C (%) D 27 | Tumor growth inhibition rate TGI (%) | Median tumor volume (mm³) D 27 | Tumor growth inhibition rate TGI (%) | Median tumor weight (g) D 27 | Tumor growth inhibition rate TGI (%) | Tumor formation rate (%) |
|---|---|---|---|---|---|---|---|---|
| 5C10H2L2-IgG1mt (5 mg/kg) | 600.6 | 24.2 | 75.8 | 0.0 | 100.0 | 0.0 | 100.0 | 40.0 |
| 5C10H2L2-IgG1mt (15 mg/kg) | 780.6 | 31.4 | 68.6 | 0.0 | 100.0 | 0.0 | 100.0 | 40.0 |
| Tecentriq ® (15 mg/kg) | 867.2 | 34.9 | 65.1 | 132.0 | 93.8 | 0.2 | 93.7 | 50.0 |

Note:
Mice were randomly grouped and the first administration was on D 0. D 27 means the 27th day after first administration.

The TGI rates of 1.5, 5 and 15 mg/kg 5C10H2L2-IgG1mt on subcutaneous xenografts of MC-38/H-11 were 63.9%, 75.8% and 68.6%, respectively calculated by the average tumor volume. Given the individual variation of tumor size in each group was very big, it was reasonable to use median tumor volume for tumor growth inhibition calculation. Under this condition, the TGI rates were 100%, 100% and 100%. The reference drug Tecentriq® (15 mg/kg) had a TGI of 93.8% (calculated with median tumor volume). The TGI of 5C10H2L2-IgG1mt (1.5, 5, 15 mg/kg) to MC-38/H-11 were 100%, 100% and 100% if calculated by median tumor weight. The TGI of Tecentriq® was 93.7%. The TGIs calculated with median tumor volume and median tumor weight are highly consistent, indicating the reliability of the calculation by tumor volume. 5C10H2L2-IgG1mt (1.5, 5, 15 mg/kg) not only inhibited tumor growth but also inhibited tumorigenesis. At the end of the experiment (D27), the tumor incidence rate of 1.5, 5, 15 mg/kg 5C10H2L2-IgG1mt were 40%, 40% and 40%, respectively. The tumor incidence rate of the Tecentriq® group was 50%. All drugs are well tolerated in the tumor bearing mice with no significant weight loss nor other symptoms observed. Compared with Tecentriq®, 5C10H2L2-IgG1mt (1.5, 5, 15 mg/kg) had stronger anti-tumor effect on colon cancer cell MC-38/H-11 subcutaneous transplantation model.

Example 19

In Vivo Tumor Inhibition Effects on Lung Cancer

Method of animal modeling: NOG mice were subcutaneously inoculated with non-small cell lung cancer cells HCC827 (purchased from ATCC Cat. No. CRL-2868). When the tumor volume reached 100 mm³, mice were then injected intravenously with activated human PBMCs to mimic human immune system before administration.

Dosing scheme: 10 mg/kg, intravenous injection, once every two days, a total of 4 times. The tumor volume was measured twice a week after administration. Mice were divided into three groups: control (IgG), 5C10H2L2-IgG1mt and Tecentriq®, each group with 6 mice.

Figure 28:
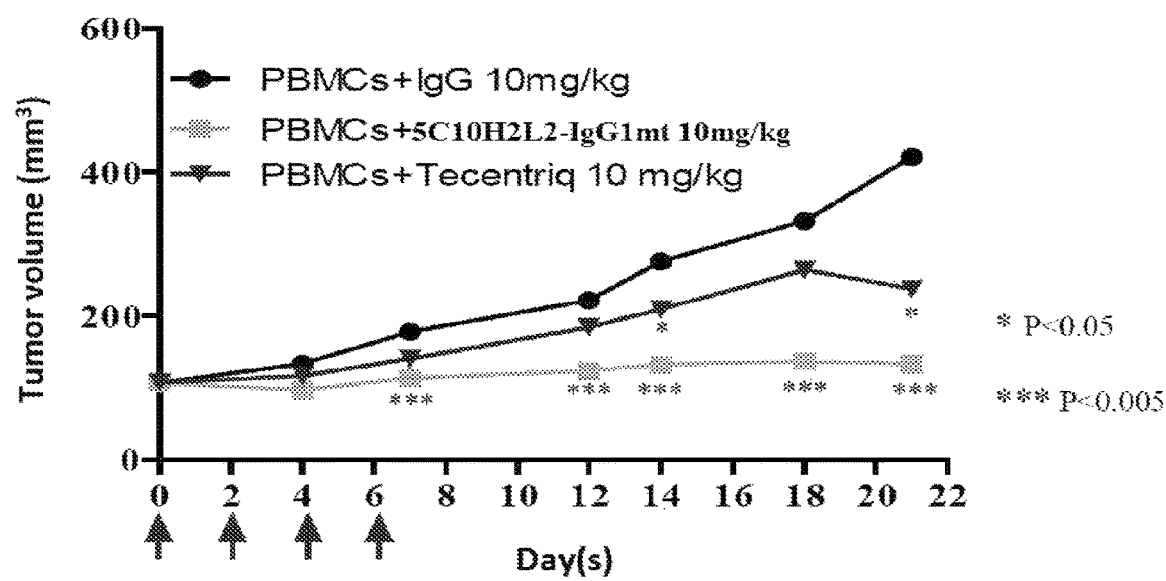
FIG. 28 Curative effect of 5C10H2L2-IgG1mt to Non small cell lung cancer cells.

The tumor growth curve is shown in FIG. 28.

The results showed that the tumor volume of 5C10H2L2-IgG1mt group was obviously smaller than that of Tecentriq® group and IgG control group from day 4 on. The tumor growth of 5C10H2L2-IgG1mt group was almost completely inhibited. In contrast, the tumors in Tecentriq® group and IgG control group grew continuously. The results demonstrated that the antibody of the present invention had a stronger in vivo antitumor effect than Tecentriq®.

While specific embodiments of the present invention have been described in detail, those skilled in the art will appreciate. According to all details that have been disclosed, various modifications and substitutions can be made to these details, which are still within the protection scope of the present invention. The full scope of the invention is given by the appended claims and any equivalents thereof.

What is claimed is:

1. An anti-PDL-1 monoclonal antibody, wherein said monoclonal antibody comprises:
   (1) A heavy chain variable region (VH) comprising an amino acid sequence of SEQ ID NO: 2, and a light chain variable region (VL) comprising an amino acid sequence of SEQ ID NO: 4;
   (2) A heavy chain variable region (VH) comprising an amino acid sequence of SEQ ID NO: 6, and a light chain variable region (VL) comprising an amino acid sequence of SEQ ID NO: 8;
   (3) A heavy chain variable region (VH) comprising an amino acid sequence of SEQ ID NO: 6, and a light chain variable region (VL) comprising an amino acid sequence of SEQ ID NO: 12;
   (4) A heavy chain variable region (VH) comprising an amino acid sequence of SEQ ID NO: 10, and a light chain variable region (VL) comprising an amino acid sequence of SEQ ID NO: 8; or
   (5) A heavy chain variable region (VH) comprising an amino acid sequence of SEQ ID NO: 10, and a light chain variable region (VL) comprising an amino acid sequence of SEQ ID NO: 12;
   wherein the heavy chain constant region of any of (1)-(5) comprises Ig gamma-1 chain constant region, ACCESSION: P01857, the light chain constant region of any of (1)-(5) comprises Ig kappa chain constant region, ACCESSION: P01834.

2. The anti-PDL-1 monoclonal antibody according to claim 1, wherein the anti-PDL-1 monoclonal antibody binds to PDL-1 with an $EC_{50}$ less than 100 nM, determined by indirect ELISA method.

3. The anti-PDL-1 monoclonal antibody according to claim 1, wherein the anti-PDL-1 monoclonal antibody comprises a mutated human IgG1 constant region.

4. The anti-PDL-1 monoclonal antibody according to claim 3, wherein the mutated human IgG1 constant region comprises at least one mutation at position 234, 235 or 237 in accordance with the EU numbering system, and the dynamic affinity of the antibody to FcγRIIIa and/or C1q is lowered after mutation.

5. The anti-PDL-1 monoclonal antibody according to claim 3, wherein the mutated human IgG1 constant region comprises 1, 2 or 3 mutations at position 234, 235 and/or 237 in accordance with the EU numbering system, and wherein the mutations are selected from the group consisting of: L234A, L235A and G237A.

6. The anti-PDL-1 monoclonal antibody according to claim 3, wherein the mutated human IgG1 constant region comprises three mutations at position 234, 235 and 237 in accordance with the EU numbering system, and wherein the mutations are L234A, L235A and G237A.

7. The anti-PDL-1 monoclonal antibody according to claim 3, wherein the mutated human IgG1 constant region comprises an N297A mutation in accordance with the EU numbering system.

8. The anti-PDL-1 monoclonal antibody according to claim 7, wherein the mutated human IgG1 constant region comprises at least one mutation at position 234, 235 or 237 in accordance with the EU numbering system, and the dynamic affinity of the antibody to FcγRIIIa and/or C1q is lowered after mutation.

9. The anti-PDL-1 monoclonal antibody according to claim 7, wherein the mutated human IgG1 constant region comprises 1, 2 or 3 mutations at position 234, 235 and/or 237 in accordance with the EU numbering system, and wherein the mutations are selected from the group consisting of: L234A, L235A and G237A.

10. The anti-PDL-1 monoclonal antibody according to claim 3, wherein the mutated human IgG1 constant region reduces ADCC activity and/or CDC activity as compared to a corresponding antibody that has a wild-type human IgG1 constant region.

11. An expression vector, which comprises an isolated nucleic acid encoding a heavy chain variable region (VH) of a monoclonal antibody, and an isolated nucleic acid encoding a light chain variable region (VL) of the monoclonal antibody; wherein said VH comprising heavy chain complementarity determining region (HCDR)1 as set forth in SEQ ID NO: 15, HCDR2 as set forth in SEQ ID NO: 16, and HCDR3 as set forth in SEQ ID NO: 17; said VL comprising light chain complementarity determining region (LCDR)1 as set forth in SEQ ID NO: 18, LCDR2 as set forth in SEQ ID NO: 19, and LCDR3 as set forth in SEQ ID NO: 20.

12. The expression vector of claim 11, wherein the nucleic acid encoding a heavy chain variable region of a monoclonal antibody encodes an amino acid sequence of SEQ ID NO: 2, SEQ ID NO: 6 or SEQ ID NO: 10; and the nucleic acid encoding a light chain variable region of said monoclonal antibody encodes an amino acid sequence of SEQ ID NO: 4, SEQ ID NO: 8 or SEQ ID NO: 12.

13. The expression vector of claim 11 wherein the nucleic acid encoding a heavy chain variable region of a monoclonal antibody comprises a nucleotide sequence selected from SEQ ID NO: 1, SEQ ID NO: 5 or SEQ ID NO: 9, and the nucleic acid encoding a light chain variable region of said monoclonal antibody comprises a nucleotide sequence selected from SEQ ID NO: 3, SEQ ID NO: 7 or SEQ ID NO:11.

14. A host cell, comprising the expression vector of claim 11.

15. A method for preparing an anti-PDL-1 monoclonal antibody, comprising the steps of:
    (i) culturing the host cell of claim 14 under a suitable condition, and
    (ii) recovering the anti-PDL-1 monoclonal antibody from the cell culture medium.

16. A conjugate, which comprises an anti-PDL-1 monoclonal antibody, and a coupling part, wherein said anti- PDL-1 monoclonal antibody is the anti-PDL-1 monoclonal antibody of claim 1 or claim 6, and wherein the coupling part is a detectable label.

17. The conjugate according to claim 16, wherein the coupling part comprises a radioactive isotope, a fluorescent substance, a luminescent substance, a colored material or an enzyme.

18. A bifunctional antibody conjugate, which comprises an anti-PDL-1 monoclonal antibody, and a conjugated part, wherein said antibody is the anti-PDL-1 monoclonal antibody of claim 1 or claim 6, and the conjugated part is a second biological functional fragment.

19. The bifunctional antibody conjugate according to claim 18, wherein the second biological functional fragment has binding activity, and is a protein, a polyethylene glycol (PEG), a nuclide, a nucleic acid, a small molecule toxin, a receptor or a ligand.

20. A multispecific antibody, which is formed by conjugation of a first antibody or fragment thereof with an additional antibody or fragment thereof or with an antibody mimetic, wherein the first antibody is the anti-PDL-1 monoclonal antibody of claim 1 or 6.

21. The multispecific antibody according to claim 20, wherein the multispecific antibody is a bispecific antibody or a tri-specific antibody or a tetra-specific antibody.

22. A kit, which comprises the anti-PDL-1 monoclonal antibody of claim 1 or 6.

23. The kit according to claim 22, wherein the kit further comprises a secondary antibody that specifically recognizes the anti-PDL-1 monoclonal antibody.

24. A method for manufacturing a kit, comprising a step of incorporating the anti-PDL-1 monoclonal antibody of claim 1 or 6 as a component of the kit, wherein the kit is for detecting the existence or level of PDL-1 in a sample.

25. A pharmaceutical composition, which comprises the anti-PDL-1 monoclonal antibody of claim 1 or 6.

26. The pharmaceutical composition according to claim 25, wherein the pharmaceutical composition further comprises a pharmaceutically acceptable carrier and/or an excipient.

27. A pharmaceutical composition, which comprises the conjugate of claim 16.

28. A pharmaceutical composition, which comprises the bifunctional antibody conjugate of claim 18.

29. A pharmaceutical composition, which comprises the multispecific antibody of claim 20.

30. A method of treatment and/or prophylaxis of a tumor expressing PDL-1, comprising a step of administering to a subject in need thereof with an effective amount of the anti-PDL-1 monoclonal antibody of claim 1 or 6.

31. The method according to claim 30, wherein said tumor is selected from breast cancer, lung cancer, liver cancer, gastric cancer, colorectal cancer, esophageal cancer, ovarian cancer, cervical cancer, kidney cancer, prostate cancer, bladder cancer, pancreatic cancer, glioma, melanoma and leukemia.

32. The method according to claim 31, wherein said lung cancer is non-small cell lung cancer.

33. The method according to claim 31, wherein said colorectal cancer is colon cancer or rectal cancer.

34. A method of treatment and/or prophylaxis of a tumor expressing PDL-1, comprising a step of administering to a subject in need thereof with an effective amount of the conjugate of claim 16.

35. A method of treatment and/or prophylaxis of a tumor expressing PDL-1, comprising a step of administering to a subject in need thereof with an effective amount of the bifunctional antibody conjugate of claim 18.

36. A method of treatment and/or prophylaxis of a tumor expressing PDL-1, comprising a step of administering to a subject in need thereof with an effective amount of the multispecific antibody of claim 20.

37. An in vivo or in vitro method, comprising a step of administering to a cell an effective amount of the anti-PDL-1 monoclonal antibody of claim 1 or 6, wherein the method comprises
   a) blocking binding of PDL-1 to PD-1 or to B7-1;
   b) downregulating PDL-1 activity or a PDL-1 level;
   c) removing immune suppression by PD-1 or by PDL-1; or
   d) enhancing expression of IFN-γ and/or IL-2 by a T lymphocyte.

38. An in vivo or in vitro method, comprising a step of administering to a cell an effective amount of the conjugate of claim 16, wherein the method comprises
   a) blocking binding of PDL-1 to PD-1 or to B7-1;
   b) downregulating PDL-1 activity or a PDL-1 level;
   c) removing immune suppression by PD-1 or by PDL-1; or
   d) enhancing expression of IFN-γ and/or IL-2 by a T lymphocyte.

39. An in vivo or in vitro method, comprising a step of administering to a cell an effective amount of the bifunctional antibody conjugate of claim 18, wherein the method comprises
   a) blocking binding of PDL-1 to PD-1 or to B7-1;
   b) downregulating PDL-1 activity or a PDL-1 level;
   c) removing immune suppression by PD-1 or by PDL-1; or
   d) enhancing expression of IFN-γ and/or IL-2 by a T lymphocyte.

40. An in vivo or in vitro method, comprising a step of administering to a cell an effective amount of the multispecific antibody of claim 20, wherein the method comprises
   a) blocking binding of PDL-1 to PD-1 or to B7-1;
   b) downregulating PDL-1 activity or a PDL-1 level;
   c) removing immune suppression by PD-1 or by PDL-1; or
   d) enhancing expression of IFN-γ and/or IL-2 by a T lymphocyte.

* * * * *

SEQUENCE LISTING

<160> NUMBER OF SEQ ID NOS: 40

<210> SEQ ID NO 1
<211> LENGTH: 360
<212> TYPE: DNA
<213> ORGANISM: Artificial
<220> FEATURE:
<223> OTHER INFORMATION: Nucleotide sequence encoding VH of antibody
      5C10

<400> SEQUENCE: 1
caggtgcaac tgaaggagtc aggacctggc ctggtggcgc cctcacagaa cctgtccatt      60
acctgcactg tctctgggtt ctcattaagc aactatgata taagctggat tcgccagcca     120
ccaggaaagg gtctggagtg gctcggagta atatggactg gtggagccac aaattataat     180
tcagctttca tgtccagact gagcatcagt agggacaact ccaagagcca agttttctta     240

```
aaaatgaaca gtctgcaaac tgatgacaca gccatatatt actgtgtgag agattcgaac    300
tataggtacg acgagccgtt tacttactgg ggccaaggga ctctggtcac tgtctctgca    360
```

<210> SEQ ID NO 2
<211> LENGTH: 120
<212> TYPE: PRT
<213> ORGANISM: Artificial
<220> FEATURE:
<223> OTHER INFORMATION: Amino acid sequence of VH of antibody 5C10

<400> SEQUENCE: 2

```
Gln Val Gln Leu Lys Glu Ser Gly Pro Gly Leu Val Ala Pro Ser Gln
1               5                   10                  15

Asn Leu Ser Ile Thr Cys Thr Val Ser Gly Phe Ser Leu Ser Asn Tyr
            20                  25                  30

Asp Ile Ser Trp Ile Arg Gln Pro Pro Gly Lys Gly Leu Glu Trp Leu
        35                  40                  45

Gly Val Ile Trp Thr Gly Gly Ala Thr Asn Tyr Asn Ser Ala Phe Met
    50                  55                  60

Ser Arg Leu Ser Ile Ser Arg Asp Asn Ser Lys Ser Gln Val Phe Leu
65                  70                  75                  80

Lys Met Asn Ser Leu Gln Thr Asp Asp Thr Ala Ile Tyr Tyr Cys Val
                85                  90                  95

Arg Asp Ser Asn Tyr Arg Tyr Asp Glu Pro Phe Thr Tyr Trp Gly Gln
            100                 105                 110

Gly Thr Leu Val Thr Val Ser Ala
        115                 120
```

<210> SEQ ID NO 3
<211> LENGTH: 318
<212> TYPE: DNA
<213> ORGANISM: Artificial
<220> FEATURE:
<223> OTHER INFORMATION: Nucleotide sequence encoding VL of antibody
      5C10

<400> SEQUENCE: 3

```
gacatcttgc tgactcagtc tccagccatc ctgtctgtga gtccaggaga aagagtcagt    60
ctctcctgca gggccagtca gagcattggc acaaacatac actggtttca gcaagaaca    120 aatggttctc caaggcttct cataaagtat gcttctgagt ctatctctgg atcccttcc    180 aggtttagtg gcagtggatc aggacagat tttactctta gcatcaacag tgtggagtct    240
gaagatattg cagattacta ctgtcaacaa agtaatagct ggccgtacac gttcggaggg    300
gggaccaagc tggaaata                                                  318
```

<210> SEQ ID NO 4
<211> LENGTH: 106
<212> TYPE: PRT
<213> ORGANISM: Artificial
<220> FEATURE:
<223> OTHER INFORMATION: Amino acid sequence of VL of antibody 5C10

<400> SEQUENCE: 4

```
Asp Ile Leu Leu Thr Gln Ser Pro Ala Ile Leu Ser Val Ser Pro Gly
1               5                   10                  15

Glu Arg Val Ser Leu Ser Cys Arg Ala Ser Gln Ser Ile Gly Thr Asn
            20                  25                  30

Ile His Trp Phe Gln Gln Arg Thr Asn Gly Ser Pro Arg Leu Leu Ile
```

```
                35                  40                  45
Lys Tyr Ala Ser Glu Ser Ile Ser Gly Ile Pro Ser Arg Phe Ser Gly
 50                  55                  60

Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Ser Asn Ser Trp Pro Tyr
                 85                  90                  95

Thr Phe Gly Gly Gly Thr Lys Leu Glu Ile
            100                 105
```

<210> SEQ ID NO 5
<211> LENGTH: 360
<212> TYPE: DNA
<213> ORGANISM: Artificial
<220> FEATURE:
<223> OTHER INFORMATION: Nucleotide sequence of VH of antibody 5C10H1L1

<400> SEQUENCE: 5

```
caggtccagc tgcaggagtc aggccccggc ctggtgaagc ccagtgagaa cctgtcaatc     60
acctgcacag tctctggctt ctcactgagc aattacgaca tcagttggat tcgacagccc    120
cctggaaagg gcctggaatg gctgggcgtg atctggacag gcgggggcaac taactataat   180
ccagccttta aaagccggct gaccatttcc agagacaact ccaagtctca ggtgtctctg    240
aaaatgagct ccctgcaggc cgctgatacc gctgtgtact attgtgtcag ggacagcaat    300
taccgctatg atgagcccct cacatactgg gggcagggaa ctctggtgac cgtctctagt    360
```

<210> SEQ ID NO 6
<211> LENGTH: 120
<212> TYPE: PRT
<213> ORGANISM: Artificial
<220> FEATURE:
<223> OTHER INFORMATION: Amino acid sequence of VH of antibody 5C10H1L1

<400> SEQUENCE: 6

```
Gln Val Gln Leu Gln Glu Ser Gly Pro Gly Leu Val Lys Pro Ser Glu
  1               5                  10                  15

Asn Leu Ser Ile Thr Cys Thr Val Ser Gly Phe Ser Leu Ser Asn Tyr
                 20                  25                  30

Asp Ile Ser Trp Ile Arg Gln Pro Pro Gly Lys Gly Leu Glu Trp Leu
             35                  40                  45

Gly Val Ile Trp Thr Gly Gly Ala Thr Asn Tyr Asn Pro Ala Phe Lys
 50                  55                  60

Ser Arg Leu Thr Ile Ser Arg Asp Asn Ser Lys Ser Gln Val Ser Leu
 65                  70                  75                  80

Lys Met Ser Ser Leu Gln Ala Ala Asp Thr Ala Val Tyr Tyr Cys Val
                 85                  90                  95

Arg Asp Ser Asn Tyr Arg Tyr Asp Glu Pro Phe Thr Tyr Trp Gly Gln
                100                 105                 110

Gly Thr Leu Val Thr Val Ser Ser
            115                 120
```

<210> SEQ ID NO 7
<211> LENGTH: 321
<212> TYPE: DNA
<213> ORGANISM: Artificial
<220> FEATURE:
<223> OTHER INFORMATION: Nucleotide sequence encoding VL of antibody
      5C10H1L1

<400> SEQUENCE: 7

```
gaaatcgtgc tgacacagag ccctgacaca ctgagcgtga ctcccaagga gaaagtcacc    60
ctgacatgcc gggcatcaca gagcatcgga acaaacattc actggttcca gcagagacca   120
ggccagagcc ccaagctgct gatcaaatac gcctccgaat ctatcagtgg cattccttcc   180
cgattctcag gcagcgggtc cggaaccgac tttactctga ccattaactc tgtggaggct   240
gaagatgccg ctacatacta ttgccagcag tctaatagtt ggccttatac cttcggccag   300
gggacaaagc tggagatcaa a                                             321
```

<210> SEQ ID NO 8
<211> LENGTH: 107
<212> TYPE: PRT
<213> ORGANISM: Artificial
<220> FEATURE:
<223> OTHER INFORMATION: Amino acid sequence of VL of antibody 5C10H1L1

<400> SEQUENCE: 8

```
Glu Ile Val Leu Thr Gln Ser Pro Asp Thr Leu Ser Val Thr Pro Lys
  1               5                  10                  15

Glu Lys Val Thr Leu Thr Cys Arg Ala Ser Gln Ser Ile Gly Thr Asn
             20                  25                  30

Ile His Trp Phe Gln Gln Arg Pro Gly Gln Ser Pro Lys Leu Leu Ile
         35                  40                  45

Lys Tyr Ala Ser Glu Ser Ile Ser Gly Ile Pro Ser Arg Phe Ser Gly
     50                  55                  60

Ser Gly Ser Gly Thr Asp Phe Thr Leu Thr Ile Asn Ser Val Glu Ala
 65                  70                  75                  80

Glu Asp Ala Ala Thr Tyr Tyr Cys Gln Gln Ser Asn Ser Trp Pro Tyr
                 85                  90                  95

Thr Phe Gly Gln Gly Thr Lys Leu Glu Ile Lys
            100                 105
```

<210> SEQ ID NO 9
<211> LENGTH: 360
<212> TYPE: DNA
<213> ORGANISM: Artificial
<220> FEATURE:
<223> OTHER INFORMATION: Nucleotide sequence encoding VH of antibody
      5C10H2L2

<400> SEQUENCE: 9

```
caggtccagc tgcaggagtc cggccccggc ctggtgaagc cctccgagac actgtctatc    60
acctgcacag tcagcggctt ctcactgagc aactacgaca tctcctggat tcgacagccc   120
cctggaaagg gcctggaatg gctgggcgtg atctggacag gcggggcaac taactataat   180
ccagccctga atctcggct gactattagt agagacaact caaagaatca ggtgtccctg    240
aaaatgagct ccgtcaccgc cgctgataca gctgtgtact attgtgtcag ggacagcaat   300
taccgctatg atgagccctt tacctactgg gggcaggga ctctggtgac cgtctctagt    360
```

<210> SEQ ID NO 10
<211> LENGTH: 120
<212> TYPE: PRT
<213> ORGANISM: Artificial
<220> FEATURE:
<223> OTHER INFORMATION: Amino acid sequence of VH of antibody 5C10H2L2

<400> SEQUENCE: 10

```
Gln Val Gln Leu Gln Glu Ser Gly Pro Gly Leu Val Lys Pro Ser Glu
```

```
1               5                   10                  15
Thr Leu Ser Ile Thr Cys Thr Val Ser Gly Phe Ser Leu Ser Asn Tyr
            20                  25                  30

Asp Ile Ser Trp Ile Arg Gln Pro Pro Gly Lys Gly Leu Glu Trp Leu
            35                  40                  45

Gly Val Ile Trp Thr Gly Gly Ala Thr Asn Tyr Asn Pro Ala Leu Lys
    50                  55                  60

Ser Arg Leu Thr Ile Ser Arg Asp Asn Ser Lys Asn Gln Val Ser Leu
65                  70                  75                  80

Lys Met Ser Ser Val Thr Ala Ala Asp Thr Ala Val Tyr Tyr Cys Val
                85                  90                  95

Arg Asp Ser Asn Tyr Arg Tyr Asp Glu Pro Phe Thr Tyr Trp Gly Gln
                100                 105                 110

Gly Thr Leu Val Thr Val Ser Ser
            115                 120

<210> SEQ ID NO 11
<211> LENGTH: 321
<212> TYPE: DNA
<213> ORGANISM: Artificial
<220> FEATURE:
<223> OTHER INFORMATION: Nucleotide sequence encoding VL of antibody
      5C10H2L2

<400> SEQUENCE: 11
gaaatcgtgc tgacacagtc tcctgatacc ctgagcgtga ctcccaagga gaaagtcacc        60
ctgacatgca gggcatcaca gagcatcgga acaaacattc actggttcca gcagaagcca       120
ggccagagcc ccaagctgct gatcaaatac gcctccgaat ctattagtgg agtgccttcc       180
cgcttctcag gcagcgggtc cggaaccgac tttactctga ccatcaactc tgtggaggct       240
gaagatgccg ctacatacta ttgccagcag tctaatagtt ggccttatac cttcggccag       300
gggacaaagc tggagatcaa a                                                 321

<210> SEQ ID NO 12
<211> LENGTH: 107
<212> TYPE: PRT
<213> ORGANISM: Artificial
<220> FEATURE:
<223> OTHER INFORMATION: Amino acid sequence of VL of antibody 5C10H2L2

<400> SEQUENCE: 12

Glu Ile Val Leu Thr Gln Ser Pro Asp Thr Leu Ser Val Thr Pro Lys
1               5                   10                  15

Glu Lys Val Thr Leu Thr Cys Arg Ala Ser Gln Ser Ile Gly Thr Asn
            20                  25                  30

Ile His Trp Phe Gln Gln Lys Pro Gly Gln Ser Pro Lys Leu Leu Ile
            35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Val Glu Ala
65                  70                  75                  80

Glu Asp Ala Ala Thr Tyr Tyr Cys Gln Gln Ser Asn Ser Trp Pro Tyr
                85                  90                  95

Thr Phe Gly Gln Gly Thr Lys Leu Glu Ile Lys
            100                 105

<210> SEQ ID NO 13
```

<211> LENGTH: 870
<212> TYPE: DNA
<213> ORGANISM: Artificial
<220> FEATURE:
<223> OTHER INFORMATION: The DNA sequence of PDL-1

<400> SEQUENCE: 13

| | | | | | |
|---|---|---|---|---|---|
| atgaggattt | tcgccgtctt | tatctttatg | acctactggc | atctgctgaa | cgcttttact | 60 |
| gtgaccgtcc | ccaaggatct | gtatgtggtg | gagtacggaa | gcaacatgac | tatcgagtgc | 120 |
| aagttccccg | tggaaaaaca | gctggacctg | gccgctctga | ttgtctattg | ggagatggaa | 180 |
| gataagaata | tcattcagtt | tgtgcacggc | gaggaagacc | tgaaagtcca | gcatagctcc | 240 |
| tacaggcagc | gcgcccgact | gctgaaggat | cagctgtccc | tggggaacgc | agccctgcag | 300 |
| atcaccgacg | tgaaactgca | ggatgctgga | gtctacaggt | gcatgatctc | ttacggcggg | 360 |
| gctgattata | agcgcattac | agtgaaagtc | aatgcacctt | ataacaagat | caatcagaga | 420 |
| attctggtgg | tcgacccagt | gaccagtgag | cacgaactga | catgtcaggc | tgagggctac | 480 |
| cccaaggcag | aagtgatctg | gacctctagt | gatcatcagg | tcctgtcagg | aaaaaccaca | 540 |
| actaccaaca | gcaagcgaga | ggaaaaactg | ttcaatgtga | catccactct | gaggatcaac | 600 |
| acaactacca | atgagatttt | ctattgcact | tttcggagac | tggaccctga | ggaaaaccac | 660 |
| accgcagagc | tggtcatccc | agaactgcca | ctggcacacc | cacctaatga | gcgaacacac | 720 |
| ctggtcatcc | tgggagccat | tctgctgtgc | ctgggcgtcg | ctctgacttt | catttttcgg | 780 |
| ctgagaaagg | ggcggatgat | ggacgtgaaa | aagtgtggca | ttcaggatac | taactcaaaa | 840 |
| aagcagtccg | ataccatct | ggaagaaacc | | | | 870 |

<210> SEQ ID NO 14
<211> LENGTH: 290
<212> TYPE: PRT
<213> ORGANISM: Artificial
<220> FEATURE:
<223> OTHER INFORMATION: The amino acid sequence of PDL-1

<400> SEQUENCE: 14

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser

```
                    165                 170                 175
Gly Lys Thr Thr Thr Thr Asn Ser Lys Arg Glu Glu Lys Leu Phe Asn
                180                 185                 190

Val Thr Ser Thr Leu Arg Ile Asn Thr Thr Thr Asn Glu Ile Phe Tyr
            195                 200                 205

Cys Thr Phe Arg Arg Leu Asp Pro Glu Glu Asn His Thr Ala Glu Leu
210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
                260                 265                 270

Gly Ile Gln Asp Thr Asn Ser Lys Lys Gln Ser Asp Thr His Leu Glu
                275                 280                 285

Glu Thr
    290

<210> SEQ ID NO 15
<211> LENGTH: 8
<212> TYPE: PRT
<213> ORGANISM: Artificial
<220> FEATURE:
<223> OTHER INFORMATION: HCDR1

<400> SEQUENCE: 15

Gly Phe Ser Leu Ser Asn Tyr Asp
1               5

<210> SEQ ID NO 16
<211> LENGTH: 7
<212> TYPE: PRT
<213> ORGANISM: Artificial
<220> FEATURE:
<223> OTHER INFORMATION: HCDR2

<400> SEQUENCE: 16

Ile Trp Thr Gly Gly Ala Thr
1               5

<210> SEQ ID NO 17
<211> LENGTH: 14
<212> TYPE: PRT
<213> ORGANISM: Artificial
<220> FEATURE:
<223> OTHER INFORMATION: HCDR3

<400> SEQUENCE: 17

Val Arg Asp Ser Asn Tyr Arg Tyr Asp Glu Pro Phe Thr Tyr
1               5                   10

<210> SEQ ID NO 18
<211> LENGTH: 6
<212> TYPE: PRT
<213> ORGANISM: Artificial
<220> FEATURE:
<223> OTHER INFORMATION: LCDR1

<400> SEQUENCE: 18

Gln Ser Ile Gly Thr Asn
1               5
```

```
<210> SEQ ID NO 19
<211> LENGTH: 3
<212> TYPE: PRT
<213> ORGANISM: Artificial
<220> FEATURE:
<223> OTHER INFORMATION: LCDR2

<400> SEQUENCE: 19

Tyr Ala Ser
1

<210> SEQ ID NO 20
<211> LENGTH: 9
<212> TYPE: PRT
<213> ORGANISM: Artificial
<220> FEATURE:
<223> OTHER INFORMATION: LCDR3

<400> SEQUENCE: 20

Gln Gln Ser Asn Ser Trp Pro Tyr Thr
1               5

<210> SEQ ID NO 21
<211> LENGTH: 117
<212> TYPE: PRT
<213> ORGANISM: Artificial
<220> FEATURE:
<223> OTHER INFORMATION: Amino acid sequence of VH of antibody 5F10

<400> SEQUENCE: 21

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asp Ile Lys Asp Thr
            20                  25                  30

Tyr Ile His Trp Val Lys Gln Arg Pro Glu Gln Gly Leu Glu Trp Ile
        35                  40                  45

Gly Arg Ile Asp Pro Ala Asp Gly Asn Thr Arg Tyr Asp Pro Lys Phe
    50                  55                  60

Gln Asp Lys Thr Thr Ile Thr Thr Asp Thr Ser Ser Asn Thr Ala His
65                  70                  75                  80

Leu Gln Leu Ser Ser Leu Thr Ser Glu Asp Thr Ala Val Tyr Tyr Cys
                85                  90                  95

Ala Arg Gly Leu Gly Ala Trp Phe Ala Ser Trp Gly Gln Gly Thr Leu
            100                 105                 110

Val Thr Val Ser Ala
        115

<210> SEQ ID NO 22
<211> LENGTH: 351
<212> TYPE: DNA
<213> ORGANISM: Artificial
<220> FEATURE:
<223> OTHER INFORMATION: Nucleotide sequence encoding VL of antibody
      5F10

<400> SEQUENCE: 22
gaggttcagc tgcagcagtc tggggcagag cttgtgaagc caggggcctc agtcaagttg      60
tcctgcacag cttctggctt cgacattaaa gacacctata tccactgggt gaagcagagg     120
cctgaacagg gcctggagtg gattggaagg attgatcctg cggacggtaa tactaggtat     180
gacccgaagt tccaggacaa gaccactata acaaccgaca catcctccaa cacagcccac     240
ctgcagctca gcagcctgac atctgaggac actgccgtct attactgtgc tagaggcctc     300
```

```
ggagcttggt tgcttcctg gggccaaggg actctggtca ctgtctctgc a            351
```

```
<210> SEQ ID NO 23
<211> LENGTH: 106
<212> TYPE: PRT
<213> ORGANISM: Artificial
<220> FEATURE:
<223> OTHER INFORMATION: Amino acid sequence of VL of antibody 5F10

<400> SEQUENCE: 23
```

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Thr Asn Ser
            20                  25                  30

Leu Asn Trp Tyr Gln Gln Lys Pro Asp Gly Thr Val Lys Leu Leu Ile
        35                  40                  45

His Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly His Thr Leu Pro Pro
                85                  90                  95

Thr Phe Gly Gly Gly Thr Lys Leu Glu Ile
            100                 105
```

```
<210> SEQ ID NO 24
<211> LENGTH: 318
<212> TYPE: DNA
<213> ORGANISM: Artificial
<220> FEATURE:
<223> OTHER INFORMATION: Nucleotide sequence encoding VL of antibody
      5F10

<400> SEQUENCE: 24
```

```
gatatccaga tgacacagac tacatcctcc ctgtctgcct ctctgggaga cagagtcacc     60
atcagttgca gggcaagtca ggacattacc aattccttaa actggtatca gcagaaacca    120
gatggaactg ttaaactcct gatccactac acatcaagat acactcagg agtcccatca     180 aggttcagtg gcagtgggtc tggaacagat tattctctca ccattagcaa cctggagcaa    240
gaagatattg ccacttactt ttgccaacag ggtcatacgc ttcctccgac gttcggtgga    300
ggcaccaagc tggaaatc                                                  318
```

```
<210> SEQ ID NO 25
<211> LENGTH: 124
<212> TYPE: PRT
<213> ORGANISM: Artificial
<220> FEATURE:
<223> OTHER INFORMATION: Amino acid sequence of VH of antibody 9F6

<400> SEQUENCE: 25
```

```
Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met Tyr Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60
```

Gln Gly Lys Ala Thr Ile Thr Ala Asp Thr Ser Ala Asn Thr Ala Tyr
65                  70                  75                  80

Leu Gln Leu Ser Ser Leu Thr Ser Glu Asp Thr Ala Val Tyr Tyr Cys
                85                  90                  95

Ser Arg Gly Pro Pro Gly Gly Ile Gly Glu Tyr Ile Tyr Ala Met Asp
            100                 105                 110

Tyr Trp Gly Gln Gly Thr Ser Val Thr Val Ser Ser
        115                 120

<210> SEQ ID NO 26
<211> LENGTH: 372
<212> TYPE: DNA
<213> ORGANISM: Artificial
<220> FEATURE:
<223> OTHER INFORMATION: Nucleotide sequence encoding VH of antibody 9F6

<400> SEQUENCE: 26
gaggttcagc tgcagcagtc tggggcagag cttgtgaagc caggggcctc agtcaagttg     60
tcctgcacag cttctggctt caacattaaa gacacctata tgtactgggt gaagcagagg    120
cctgaacagg gcctggagtg gattggaagg attgatcctg cgaatggtaa tactaaatat    180
gacccgaagt tccagggcaa ggccactata acagcagaca catccgccaa cacagcctac    240
ctgcagctca gcagcctgac atctgaggac actgccgtct attactgttc tagaggccct    300
ccaggaggta tcggcgagta tatctatgct atggactact ggggtcaagg aacctcagtc    360
accgtctcct ca                                                        372

<210> SEQ ID NO 27
<211> LENGTH: 107
<212> TYPE: PRT
<213> ORGANISM: Artificial
<220> FEATURE:
<223> OTHER INFORMATION: Amino acid sequence of VL of antibody 9F6

<400> SEQUENCE: 27

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Pro Thr Phe Gly Gly Gly Thr Lys Leu Glu Ile
            100                 105

<210> SEQ ID NO 28
<211> LENGTH: 321
<212> TYPE: DNA
<213> ORGANISM: Artificial
<220> FEATURE:
<223> OTHER INFORMATION: Nucleotide sequence encoding VL of antibody 9F6

<400> SEQUENCE: 28
caaattgttc tcacccagtc tccagcaatc atgtctgcat ctctagggga acgggtcacc     60

```
atgacctgca ctgccagctc aagtgtaagt tccagttact tgcactggta ccagcagaag    120
ccaggatcct cccccaaact ctggatttat agcacatcca acctggcttc tggagtccca    180
gctcgcttca gtggcagtgg gtctgggacc tcttactctc tcacaatcag cagcatggag    240
gctgaagatg ctgccactta ttactgccac cagtatcatc gttcccccacc cacgttcggt    300 ggaggcacca agctggaaat c                                              321
```

<210> SEQ ID NO 29
<211> LENGTH: 8
<212> TYPE: PRT
<213> ORGANISM: Artificial
<220> FEATURE:
<223> OTHER INFORMATION: HCDR1

<400> SEQUENCE: 29

Gly Phe Asp Ile Lys Asp Thr Tyr
1               5

<210> SEQ ID NO 30
<211> LENGTH: 8
<212> TYPE: PRT
<213> ORGANISM: Artificial
<220> FEATURE:
<223> OTHER INFORMATION: HCDR2

<400> SEQUENCE: 30

Ile Asp Pro Ala Asp Gly Asn Thr
1               5

<210> SEQ ID NO 31
<211> LENGTH: 10
<212> TYPE: PRT
<213> ORGANISM: Artificial
<220> FEATURE:
<223> OTHER INFORMATION: HCDR3

<400> SEQUENCE: 31

Ala Arg Gly Leu Gly Ala Trp Phe Ala Ser
1               5                   10

<210> SEQ ID NO 32
<211> LENGTH: 6
<212> TYPE: PRT
<213> ORGANISM: Artificial
<220> FEATURE:
<223> OTHER INFORMATION: LCDR1

<400> SEQUENCE: 32

Gln Asp Ile Thr Asn Ser
1               5

<210> SEQ ID NO 33
<211> LENGTH: 3
<212> TYPE: PRT
<213> ORGANISM: Artificial
<220> FEATURE:
<223> OTHER INFORMATION: LCDR2

<400> SEQUENCE: 33

Tyr Thr Ser
1

<210> SEQ ID NO 34
<211> LENGTH: 9
<212> TYPE: PRT

```
<213> ORGANISM: Artificial
<220> FEATURE:
<223> OTHER INFORMATION: LCDR3

<400> SEQUENCE: 34

Gln Gln Gly His Thr Leu Pro Pro Thr
1               5

<210> SEQ ID NO 35
<211> LENGTH: 8
<212> TYPE: PRT
<213> ORGANISM: Artificial
<220> FEATURE:
<223> OTHER INFORMATION: HCDR1

<400> SEQUENCE: 35

Gly Phe Asn Ile Lys Asp Thr Tyr
1               5

<210> SEQ ID NO 36
<211> LENGTH: 8
<212> TYPE: PRT
<213> ORGANISM: Artificial
<220> FEATURE:
<223> OTHER INFORMATION: HCDR2

<400> SEQUENCE: 36

Ile Asp Pro Ala Asn Gly Asn Thr
1               5

<210> SEQ ID NO 37
<211> LENGTH: 17
<212> TYPE: PRT
<213> ORGANISM: Artificial
<220> FEATURE:
<223> OTHER INFORMATION: HCDR3

<400> SEQUENCE: 37

Ser Arg Gly Pro Pro Gly Gly Ile Gly Glu Tyr Ile Tyr Ala Met Asp
1               5                   10                  15

Tyr

<210> SEQ ID NO 38
<211> LENGTH: 7
<212> TYPE: PRT
<213> ORGANISM: Artificial
<220> FEATURE:
<223> OTHER INFORMATION: LCDR1

<400> SEQUENCE: 38

Ser Ser Val Ser Ser Ser Tyr
1               5

<210> SEQ ID NO 39
<211> LENGTH: 3
<212> TYPE: PRT
<213> ORGANISM: Artificial
<220> FEATURE:
<223> OTHER INFORMATION: LCDR2

<400> SEQUENCE: 39

Ser Thr Ser
1

<210> SEQ ID NO 40
<211> LENGTH: 9
```

```
<212> TYPE: PRT
<213> ORGANISM: Artificial
<220> FEATURE:
<223> OTHER INFORMATION: LCDR3

<400> SEQUENCE: 40

His Gln Tyr His Arg Ser Pro Pro Thr
1               5
```